United States Patent
Feng et al.

(10) Patent No.: US 10,898,080 B2
(45) Date of Patent: Jan. 26, 2021

(54) MICROCIRCULATION SHOCK MONITOR ENABLING RAPID AND REPEATED POSITIONING, MONITORING SYSTEM AND MONITORING METHOD

(71) Applicant: Xinghuai Feng, Jiangsu (CN)

(72) Inventors: Xinghuai Feng, Jiangsu (CN); Xiaoping Zhang, Jiangsu (CN)

(73) Assignee: Xinghuai Feng, Jiangsu (CN)

( * ) Notice: Subject to any disclaimer, the term of this patent is extended or adjusted under 35 U.S.C. 154(b) by 238 days.

(21) Appl. No.: 16/017,385

(22) Filed: Jun. 25, 2018

(65) Prior Publication Data

US 2018/0303352 A1 Oct. 25, 2018

Related U.S. Application Data

(63) Continuation of application No. PCT/CN2017/070249, filed on Jan. 5, 2017.

(30) Foreign Application Priority Data

Jan. 12, 2016 (CN) .......................... 2016 1 0016754

(51) Int. Cl.
*A61B 5/02* (2006.01)
*A61B 5/026* (2006.01)
(Continued)

(52) U.S. Cl.
CPC .......... *A61B 5/02007* (2013.01); *A61B 5/004* (2013.01); *A61B 5/0088* (2013.01);
(Continued)

(58) Field of Classification Search
CPC ... A61B 5/02007; A61B 5/4552; A61B 5/004; A61B 5/0088; A61B 5/026; A61B 5/412;
(Continued)

(56) References Cited

U.S. PATENT DOCUMENTS

2006/0184037 A1* 8/2006 Ince ..................... A61B 1/0607
600/476
2011/0190612 A1 8/2011 McKenna et al.
2016/0313546 A1* 10/2016 Feldman ............... G01J 3/0256

FOREIGN PATENT DOCUMENTS

CN 1938626 A 3/2007
CN 201508434 U 6/2010
(Continued)

OTHER PUBLICATIONS

Edul, Vanina S Kanoore; Enrico Carolina; Laviolle, Bruno; Vazquez, Alejandro Risso; Ince, Can; Dubin, Arnaldo. Quantitative assessment of the microcirculation in healthy volunteers and in patients with septic shock. Crit. Care Med. May 31, 2012, vol. 40, No. 5, pp. 1443-1448, ISSN 0090-3493. (Year: 2012).*

(Continued)

*Primary Examiner* — Christine H Matthews
*Assistant Examiner* — Joshua Daryl D Lannu
(74) *Attorney, Agent, or Firm* — Wayne & Ken, LLC; Tony Hom

(57) ABSTRACT

The present invention discloses a microcirculation shock monitor enabling rapid and repeated positioning, a monitoring system and a monitoring method, belonging to the technical field of microcirculation shock monitoring. By the present invention, the same blood vessel in the same monitored area can be repeatedly positioned and monitored quickly within different periods of time, and blood vessel image data can be acquired, and then, on this basis, qualitative analysis or quantitative analysis is performed to obtain related monitored data, where quantitative analysis parameters comprise a high-speed blood flow intensity ratio R, a high-speed blood flow spreading rate S, a high-speed blood flow intensity duration T and a difference D of abnormal change in high-speed blood flow intensity of a monitored object, which facilitates studies and lays an accurate data (Continued)

foundation for rapidly indicating early and middle stage indications of infectious shock in a next step.

11 Claims, 10 Drawing Sheets

(51) Int. Cl.
*A61B 5/00* (2006.01)
*G06T 7/00* (2017.01)
*G02B 21/36* (2006.01)
*G02B 21/00* (2006.01)

(52) U.S. Cl.
CPC .............. *A61B 5/026* (2013.01); *A61B 5/412* (2013.01); *A61B 5/4552* (2013.01); *G02B 21/0008* (2013.01); *G02B 21/365* (2013.01); *G06T 7/0014* (2013.01); *G06T 2207/30104* (2013.01)

(58) Field of Classification Search
CPC .............. G02B 21/365; G02B 21/0008; G02B 21/361; G02B 21/0012; G06T 2207/30104; G06T 7/0014
See application file for complete search history.

(56) References Cited

FOREIGN PATENT DOCUMENTS

| | | |
|---|---|---|
| CN | 201765375 U | 3/2011 |
| CN | 102389291 A | 3/2012 |
| CN | 103439788 A | 12/2013 |
| CN | 104783767 A | 7/2015 |
| CN | 205251518 U | 5/2016 |
| CN | 105662388 A | 6/2016 |
| WO | 2011097291 A1 | 8/2011 |

OTHER PUBLICATIONS

Quantitative assessment of the microcirculation in healthy volunteers and in patients with septic shock Vanina S. Kanoore Edul, MD; Carolina Enrico, MD; Bruno Laviolle, MD, PhD; Alejandro Risso Vazquez, MD; Can Ince, PhD; Arnaldo Dubin, MD, PhD.

* cited by examiner

MICROCIRCULATION SHOCK MONITOR ENABLING RAPID AND REPEATED POSITIONING, MONITORING SYSTEM AND MONITORING METHOD

TECHNICAL FIELD

The present invention relates to a microcirculation shock monitoring system, belonging to the technical field of medical monitoring.

BACKGROUND OF THE PRESENT INVENTION

The monitoring of the sublingual mucosal microcirculation is a hot topic in researches in the intensive care medicine in the past 20 years. It mainly studies changes in the sublingual mucosal microcirculation of sepsis. Compared with the finger nailfold microcirculation, the sublingual microcirculation is richer in terms of vascular status and information indicated. For example, through study of the sublingual microcirculation, capillary arteries and veins with a diameter ranging from about 200 μm to 4 μm and single-cell capillaries can be observed. In an addition, the observable scope is much larger in the sublingual microcirculation than nail fold capillaroscopy under which only blood vessels in restricted positions of fingers can be observed. Moreover, since the sublingual mucosal microcirculation is between the heart and the brain while the nailfold microcirculation is at the ending of the human body, the sublingual mucosal microcirculation can better reflect the microcirculation conditions of internal organs.

Upon retrieval, it was found that U.S. Pat. No. 8,452,384B2 discloses systems and methods for sidestream dark field imaging. This handheld instrument uses a prime lens (4.5× or 5×) during the observation of the microcirculation of sublingual mucosa, and the actual scope observed by the instrument is only about one square millimeter (Document 5: page 5: The optical field of view of SDF imaging with 5× objectives is approximately 0.94 mm×0.75 mm). However, the area of the human sublingual mucosa is about 100 to 200 square millimeters, which is 100 to 200 times of the field of view of the instrument. In addition, the distribution and flow states of the capillary microcirculation are greatly different within different regions of the sublingual mucosa. Even for a healthy person, the observed density and flow states of capillaries at different positions are greatly different. The monitoring of changes in the sublingual mucosal microcirculation is carried out through detecting the density and flow states of the microcirculation at different time and then performing comparative analysis. Due to limitations of the instrument with prime lens, repeated observations of the same blood vessel in the same region of the sublingual microcirculation cannot be quickly performed in current clinical practice; and only blood vessels randomly picked can be observed (note: It is required to find the same blood vessel very quickly because it is not applicable to observe a patient's sublingual mucosa for too long a time due to the limits of patient's tolerance. Even if the existing instrument may happen to find the same blood vessel of the sublingual mucosa in a healthy person, good coordination from that person and sufficient search time are also required. However, it is not generally applicable for patients in clinical setting).

In the research done by the instrument with prime lens, different microcirculation areas are sampled and analyzed, producing a statistical average based on which the comparison between data gained at different time of observation can be realized. The results gained in this way are not very accurate, and too much time is spent for the process. Therefore, it cannot meet the basic requirements of rapid and accurate monitoring of sublingual microcirculation in the clinical setting, not even to mention achieving a high function of continuously rapid and accurate monitoring. Documents 1, 2, 3, 4, 5 and 8 have reflected the deficiencies of the instrument and the unanimous request from the intensive medical community for the rapidity and accuracy of the monitoring and analysis on the sublingual microcirculation.

In order to overcome the problem of inaccuracy and time consumption caused by averaging of data from different microcirculation regions, the most ideal and accurate method is to perform quick sampling repeatedly in the same sublingual area at different time, and then compare these microcirculation images of the same blood vessel/position obtained at different time of observation. However, due to the above-mentioned limits of the instrument, it is commonly agreed by the intensive medical community that it is impossible to quickly find and observe the same blood vessel at different time periods (due to the patient's intolerance, it is impossible to observe the patient's mouth for a long time). Therefore, the multi-point acquisition and averaging method has been used worldwide over past 20 years (e.g., Documents 1-5, and Document 8). At present, the major focus on improvement is to improve rapid analysis through software upgrade. Such software improvement is still based on the calculation of the average, so the goal of achieving rapidity and accuracy cannot yet be realized.

Therefore, even with software improvements, the four indicators (i.e., the high-speed blood flow intensity ratio, the high-speed blood flow spreading rate, the high-speed blood flow intensity duration and the difference of the abnormal intensity change) of the sublingual microcirculation proposed by the inventor(s) cannot be acquired and monitored.

Meanwhile, in terms of the monitoring indicators of the sublingual microcirculation, Document 5 has disclosed several indicators of the sublingual microcirculation in an international round table conference: Total Vessel Density (TVD), Perfusing Vessel Density (PVD), Proportion of Perfused vessels (PPV) and Microvascular Flow indicator (MFI) are detected at three parts of the sublingual mucosa, and then averaged; and, the step is repeated during the second time of monitoring, and the two averages are compared to eventually obtain a clinical conclusion. The four indicators are obtained when the diameter of blood vessels is less than 20 μm to 25 μm. These indicators fail to indicate the stage of infectious shock (septic shock). Particularly, these indicators do not show any specific warning indicators in the early and middle stages, which need to be urgently detected in clinical practice.

For the above limits, the existing instruments for monitoring the sublingual microcirculation can only be used in scientific research but cannot be universally applied in clinical practice.

In order to overcome the deficiencies of such instruments, the present invention is proposed on the following basis: firstly, the same blood vessel and blood vessels in the same area of the sublingual microcirculation can be quickly and repeatedly positioned at different periods of time, so as to obtain the specific indices (which will be described in detail below) of the infectious shock, and secondly, in order to monitor such indices for comparative analysis, a monitor capable of rapidly and repeatedly positioning the same blood vessel in the same area of the sublingual microcirculation is demanded, so as to obtain the specific indices of the infectious shock, and further to judge the stage of the infectious shock, accordingly, the present invention can be widely used clinically.

Sources of the documents cited above:
Document 1: The Research Progress of Microcirculation Monitoring Technology, GU Ni-na, et al., *Medical Recapitulate*, March 2015, Vol. 21, No. 5, 873-875;
Document 2: Application and Progress of Microcirculation Monitoring in Patients with Septic Shock, ZENG Xueying, et al., *Chinese Journal of Respiratory and Critical Care Medicine*, May 2014, Vol. 13, No. 3, 319-322;
Document 3: Observation of Changes of Sublingual Microcirculation in Elderly Patients With Severe Sepsis and Septic Shock, YAN Molei, et al., *National Medical Journal of China*, Jul. 2, 2013, Vol. 93, No. 25;
Document 4: The Clinical Significance of Determining the Severity and Prognosis by Monitoring the Changes in Sublingual Microcirculation in Patients with Severe Sepsis, ZHAO Mengya, et al., *Chinese Critical Care Medicine*, March 2012, Vol. 24, No. 23, 158-161;
Document 5: How to Evaluate the Microcirculation: Report of a Round Table Conference, Daniel De Backer, et al., published on Sep. 10, 2007, *Critical Care*, 2007, 11:R101 (doi:10.1186/cc6118);
Document 6: Surviving Sepsis Campaign: International Guidelines for Treatment of Severe Sepsis and Septic Shock: 2012, R. Phillip Dellinger, et al., *Critical Care Medicine*, February 2013, Vol. 41, No. 2;
Document 7: Chinese Guidelines for Management of Severe Sepsis/Septic Shock (2014), *Chinese Critical Care Medicine*, June 2015, Vol. 27, No. 6, 401-426;
Document 8: Orthogonal Polarization Spectra and Sidestream Dark Field Imaging Technology in Microcirculation of Sepsis, TANG Xue, et al., *Chinese General Practice*, 2011, Vol. 14, No. 18, 2110-2112; and
Document 9: Quantitative Assessment of the Microcirculation in Healthy Volunteers and in Patients with Septic Shock, Vanina S., et al., *Critical Care Medicine*, 2012, Vol. 40, No. 5, 1443-1448.

SUMMARY OF THE PRESENT INVENTION

To overcome the deficiencies in the prior art, the present invention provides a microcirculation shock monitor enabling rapid and repeated positioning, a monitoring system and a monitoring method, belonging to the technical field of microcirculation shock monitoring, which can repeatedly position and monitor a blood vessel in a monitored area quickly within different time periods and acquire image data of the blood vessel, and then perform qualitative analysis or quantitative analysis on this basis to obtain related monitored data. Accordingly, this facilitates further studies and lays an accurate data foundation for rapidly indicating early and middle stage of septic shock in the next step.

The present invention is realized by the following technical solutions.

A microcirculation shock monitor enabling rapid and repeated positioning is provided, including a host body, wherein a probe device is mounted at a front end of the host body; a microscope continuous zooming mechanism is mounted in the host body; a front lens and a rear lens are mounted at two ends of the microscope continuous zooming mechanism, respectively; a rear surface of the rear lens is directly connected to a camera; and, at least one zooming lens capable of reciprocating along a zooming mechanism-driving and guiding device is provided between the front lens and the rear lens.

A focusing tube is mounted in the rear of the probe device or on the front lens of the microscope continuous zooming mechanism or on the camera.

A direction adjustment mechanism and/or a parfocalization mechanism and/or a cross calibration mechanism is mounted between the microscope continuous zooming mechanism and the camera.

A probe sleeve is provided at the front end of the host body, the probe device is mounted on the probe sleeve in such a way that the probe device is movable relative to the host body in an axial direction, and an adjustment and positioning device is mounted between the probe sleeve and the probe device.

A handle is further provided on the host body allowing for holding and controlling a viewing angle.

A disposable sterile sheath is provided for the probe device. The disposable sterile sheath functions to keep an observed surface flat and avoid cross infection.

A microcirculation shock monitoring system is provided, including:
a data acquisition module configured to repeatedly position and acquire the image data of the same blood vessels in a monitored area;
a data preprocessing module configured to filter and stabilize the acquired image data of the blood vessel;
a comparison module configured to compare the stabilized measured image data of the blood vessel with reference data, to determine and analyze changes in blood flow rate in the blood vessel and/or changes in distribution density of the blood vessel; and
a storage module configured to store the measured image data of the blood vessel and the reference data in a database.

Further,
the data preprocessing module includes a blood flow rate measurement module configured to generate real-time blood flow rate data in the blood vessel;
data stored in the storage module comprises real-time and historical image data of the blood vessels obtained from the monitored patient, the average value of the highest microcirculation blood flow rates in healthy people, range of difference in blood flow rates of healthy people, and stabilized data of the above-mentioned data; and
during the comparison of images of the blood vessel, the following four quantitative analysis indicators are included:
hereinafter, all averages of highest blood flow rates are the averages of the highest blood flow rates of more than two capillaries within the field of view of the instrument; and, if there is only one capillary at the highest flow rate, the flow rate of this capillary is considered as the average (regardless of the diameter of the capillary);
i) high-speed blood flow intensity ratio which is a ratio of an average of the highest blood flow rates in sublingual microcirculation of a septic shock patient within field of view to an average of the highest flow rates in a sublingual microcirculation of a healthy person;
the high-speed blood flow intensity ratio R is expressed as R=P/N*100%;
where P is the average of the highest blood flow rates in the sublingual microcirculation of the septic shock patient within the field of view (prestissimo); and
N is the average of the highest blood flow rates in the sublingual microcirculation of the healthy person (normal); and the high-speed blood flow intensity ratio measures the high-speed blood flow intensity;

ii) high-speed blood flow spreading rate which is a ratio of the total length of all blood vessels at a high blood flow rate to the total length of all capillaries in the sublingual microcirculation of a septic shock patient within the field of view;

the high-speed blood flow spreading rate S is expressed as S=HL/TL*100%, where HL is the total length of all blood vessels at high speed blood flow rates within the field of view, and TL is the total length of all blood vessels within the same field of view; and the high-speed blood flow spreading rate measures whether the high-speed blood flow is activated completely;

iii) high-speed blood flow intensity duration (Time) which is the time interval between the time when the high-speed blood flow is found in the sublingual microcirculation of a septic shock patient for the first time and the time when the high-speed blood flow begins to decelerate;

the high-speed blood flow intensity duration T is expressed as T=T2−T1 (with respect to the same blood vessel within the same field of view), where T is the high-speed blood flow intensity duration, and T1 is the time when the high-speed blood flow is found for the first time which can also be traced and determined according to other manifestations of the patient (for example, the initial onset time or the like), T2 is the time when the high-speed blood flow begins to decelerate; and high-speed blood flow intensity duration traces the possible historical occurrence time of the high-speed blood flow and determines the possible approach time of the septic shock; and iv) difference of abnormal change in high-speed blood flow intensity which is the acceleration change before and after the high-speed blood flow in the sublingual microcirculation of a septic shock patient, i.e., abnormal acceleration or deceleration within different time periods before and after the high-speed blood flow in the sublingual microcirculation of the septic shock patient;

the difference D of the abnormal change in high-speed blood flow intensity is expressed as D=D1−D2, where D is the difference of abnormal change in high-speed blood flow intensity;

D1 is a difference of changes in highest blood flow rate of the patient with infectious shock; and D2 is a difference of changes in the highest blood flow rate of a healthy person;

the difference D1 of changes in the highest blood flow rate of the infectious shock patient is expressed as D1=P2−P1;

P2 is the last measured average of highest blood flow rates of the septic shock patient;

P1 is the previously measured average of highest blood flow rates of the septic shock patient;

if D1 is greater than 0, the blood flow rate is accelerated; if D1 is less than 0, the blood flow rate is decelerated; and if D1 is equal to 0, the blood flow rate is stable;

$$D2=P4-P3;$$

D2 is a difference of changes in highest blood flow rate of the healthy person;

P4 is the last measured average of highest blood flow rates of the healthy person;

P3 is the previously measured average of highest blood flow rates of the healthy person.

(This numerical value is generally equal to 0, the sublingual blood flow of a healthy person is generally constant when the person does not do strenuous exercise).

Because the constant state D2 of the sublingual blood flow is generally equal to 0 when a healthy person does not do strenuous exercise, the difference D of the abnormal change in high-speed blood flow intensity is actually expressed as the difference D1 of changes in highest blood flow rate of a septic shock patient. That is, D=D1−D2=D1.

The formula is simplified as follows: D=D1−D2=P2−P1, i.e., a difference between the last average and the previous average of high-speed blood flow rates of the same blood vessel in the sublingual microcirculation of the septic shock patient.

If D and D1 are greater than 0, the blood flow rate is accelerated; and, if D and D1 are less than 0, the blood flow rate is decelerated. If D and D1 are equal to 0, the flow rate is stable.

Since the blood flow rate of a healthy person is stable, P4−P3 is equal to 0. Hence, the difference D of abnormal change in high-speed blood flow intensity of the monitored object is expressed as D=D1−D2=D1=P2−P1, that is, D is equal to a difference between the last measured average P2 of highest blood flow rates of the septic shock patient and the previously measured average P1 of highest blood flow rates of the septic shock patient.

Difference of abnormal change in high-speed blood flow intensity determines the presence or absence of the high-speed blood flow and different stages of the septic shock. Since the blood flow of a healthy person is generally constant when the person does not do strenuous exercise, the abnormal acceleration and abnormal deceleration of the blood flow rate will not occur for a healthy person. If abnormal acceleration and abnormal deceleration occur, even if the blood flow rate is not very high, the fourth specific indicator of the septic shock will appear. The abnormal acceleration of the flow rate measures the start stage of the high-speed blood flow in the early stage of the septic shock, and the abnormal deceleration of the flow rate measures the middle and advanced stages of the septic shock.

Further, the storage module includes a blood flow rate quick-sampling template, and it comprises a set of blood flow rate recording templates on which flow rates are accurately marked to quickly compare and determine the blood flow rate in the real-time image data of the blood vessel.

A method for monitoring blood flow change parameters in blood vessels in the microcirculation for shock monitoring is provided, including the following methods and steps:

repeatedly positioning a blood vessel in a monitored area and acquiring image data of the blood vessel;

filtering and stabilizing the acquired image data of the blood vessel;

storing measured image data of the blood vessel and reference data in a database; and comparing the stabilized measured image data of the blood vessel with the reference data and determining and analyzing changes in blood flow rate and/or changes in distribution density of the blood vessel.

Further, in the method for monitoring blood flow change parameters in blood vessels in the microcirculation for shock monitoring, during the comparison of images of the blood vessel, using the stabilized real-time image data of the blood vessel as measured data, using the previously stabilized data of images of the same blood vessel in the same monitored area as reference data, observing with the naked eyes by an operator, and determining changes in blood flow rate in the blood vessel and/or the density change.

Further, in the method for monitoring blood flow change parameters in blood vessels in the microcirculation for shock monitoring, after the step of filtering and stabilizing the acquired image data of the blood vessel, measuring the blood flow rate to generate real-time data of the blood flow rate in the blood vessel;

data stored in the storage module comprises real-time and historical image data of the blood vessels obtained from the monitored patient, the average value of the highest microcirculation blood flow rates in healthy people, range of difference in blood flow rates of healthy people, and stabilized data of the above-mentioned data; and during the comparison of images of the blood vessel, the following four quantitative analysis indicators are included:

i) high-speed blood flow intensity ratio which is a ratio of an average of the highest blood flow rates in the sublingual microcirculation of a septic shock patient within the field of view to an average of the highest rates in a sublingual microcirculation of healthy people;

the high-speed blood flow intensity ratio R is expressed as R=P/N*100%;

where P is the average of highest (prestissimo) blood flow rates in the sublingual microcirculation of the septic shock patient within the field of view; and N is the average of highest blood flow rates in the sublingual microcirculation of the healthy person (normal); and the high-speed blood flow intensity ratio measures the high-speed blood flow intensity;

ii) high-speed blood flow spreading rate which is a ratio of the total length of all blood vessels at a high blood flow rate to the total length of all capillaries in the sublingual microcirculation of a septic shock patient within the field of view;

the high-speed blood flow spreading rate S is expressed as S=HL/TL*100%, where HL is the total length of all blood vessels of high speed blood flow rate within the field of view, and TL is the total length of all blood vessels within the same field of view; and the high-speed blood flow spreading rate measures whether the high-speed blood flow is activated completely;

iii) high-speed blood flow intensity duration which is a time interval between the time when the high-speed blood flow is found in the sublingual microcirculation of a septic shock patient for the first time and the time when the high-speed blood flow begins to decelerate;

the high-speed blood flow intensity duration T is expressed as T=T2-T1 (with respect to the same blood vessel within the same field of view), where T is the high-speed blood flow intensity duration, and T1 is the time when the high-speed blood flow is found for the first time which is traced and determined according to other manifestations of the patient (for example, the initial onset time or the like), T2 is the time when the high-speed blood flow begins to decelerate; and high-speed blood flow intensity duration traces the possible historical occurrence time of the high-speed blood flow and determines the possible approach time of the septic shock; and iv) difference of abnormal change in high-speed blood flow intensity which is the acceleration change before and after the high-speed blood flow in the sublingual microcirculation of a septic shock patient, i.e., abnormal acceleration or abnormal deceleration within different time periods before and after the high-speed blood flow in the sublingual microcirculation of the septic shock patient;

the difference D of abnormal change in high-speed blood flow intensity is expressed as D=D1-D2, where D is the difference of abnormal change in high-speed blood flow intensity;

D1 is a difference of changes in highest blood flow rate of the patient with infectious shock;

D2 is a difference of changes in highest blood flow rate of the healthy person;

the difference D1 of changes in highest blood flow rate of the infectious shock patient is expressed as D1=P2-P1;

P2 is the last measured average of the highest blood flow rates of the septic shock patient;

P1 is the previously measured average of the highest blood flow rates of the septic shock patient;

if D1 is greater than 0, the blood flow rate is accelerated; if D1 is less than 0, the blood flow rate is decelerated t; and if D1 is equal to 0, the blood flow rate is stable;

$$D2=P4-P3;$$

D2 is the difference of changes in highest blood flow rate of the healthy person;

P4 is the last measured average of highest blood flow rates of the healthy person;

P3 is the previously measured average of highest blood flow rates of the healthy person.

(This numerical value is generally equal to 0, the sublingual blood flow of a healthy person generally flows at a constant speed when the person does not do strenuous exercise).

Since the constant state D2 of the sublingual blood flow is generally equal to 0 when a healthy person does not do strenuous exercise, actually, the difference D of abnormal change in high-speed blood flow intensity is expressed as the difference D1 of changes in highest blood flow rate of the patient with infectious shock. That is, D=D1-D2=D1.

The formula is simplified as follows: D=D1-D2=P2-P1, i.e., a difference between the last average and the previous average of high-speed blood flow rates of the same blood vessel in the sublingual circulation of the septic shock patient.

If D and D1 are greater than 0, the blood flow rate is accelerated; and, if D and D1 are less than 0, the blood flow rate is decelerated. If D and D1 are equal to 0, the flow rate is stable.

Since the blood flow rate of a healthy person is stable, P4-P3 is equal to 0. Hence, the difference D of abnormal change in high-speed blood flow intensity of the monitored object is expressed as D=D1-D2=D1=P2-P1, that is, D is equal to a difference between the last measured average P2 of highest blood flow rates of the septic shock patient and the previously measured average P1 of highest blood flow rates of the septic shock patient.

This difference of abnormal change in high-speed blood flow intensity determines the presence or absence of the high-speed blood flow and different stages of the septic shock. Since the blood flow of a healthy person is generally constant when the person does not do strenuous exercise, the abnormal acceleration and abnormal deceleration of the blood flow rate will not occur for a healthy person. If abnormal acceleration and abnormal deceleration occur, even if the blood flow rate is not very high, the fourth specific indicator of the septic shock will appear. The abnormal acceleration of the flow rate measures the start stage of the high-speed blood flow in the early stage of the septic shock, and the abnormal deceleration of the flow rate measures the middle and advanced stages of the septic shock.

The present invention has the following beneficial effects.

The rapid and accurate comparison and monitoring of the sublingual microcirculation is always a goal expected to be achieved in the intensive care medicine (Documents 1, 2 and 8). In the present invention, by providing a microscope continuous zooming mechanism in the sublingual microcirculation shock monitor, the rapid and repeatable positioning function is supported. The original monitored target can be found within 2 to 3 seconds for accurate comparison. The traditional inaccurate and labor-and-time-consuming method in which averages at multiple points are analyzed can be replaced with this method. The long-standing technical challenge is solved and the goal expected to be achieved in the intensive medical community is achieved.

The four specific indicators (four indicators for short, i.e., the high-speed blood flow intensity, similarity, duration and changes in rate) in the present invention can be used as indicators for indicating the early and middle stages of the septic shock. However, at present, the sublingual microcirculation indicators used in China and foreign countries cannot expressly indicate the early and middle stages of the septic shock.

In the present invention, the same blood vessel in a monitored area can be repeatedly positioned, and image data of the blood vessel can be acquired; and then, on this basis, qualitative analysis or quantitative analysis is performed to obtain related monitoring data. Accordingly, this facilitates studies and lays an accurate data foundation for rapidly indicating early and middle stage indications of septic shock in the next step.

Overall, the combination of following three, i.e. the microcirculation shock monitor enabling rapid and repeated positioning, the complete monitoring system and the monitoring method of the present invention meets eight ideal requirements on the rapidity, simplicity, non-invasion, continuity, accuracy, specificity, effectiveness and safety of the shock monitoring. A clinically practical monitor and a monitoring system and method are provided for the septic shock.

For the reasons described at the beginning of the article, the existing instruments for monitoring the sublingual microcirculation can only be used in scientific research, but cannot be universally applied in clinical practice. The instrument of the present invention is provided to solve the problem and remove the barriers to clinical application. Like sphygmomanometers and stethoscopes, the instrument of the present invention can also be conveniently used to carry out routine check on patients so as to determine suspected patients. Accordingly, the mortality rate of the dangerous septic shock can be reduced greatly, thereby bringing about a remarkable technical progress and bringing benefits to mankind.

In addition, since the probe device of the present invention can be moved relative to the host body along the axial direction of the probe and stay in a fixed position, various states of the probe in contact with the observed object can be allowed. When it is not allowed to closely touch the surface of the observed object (e.g., the rat craniocerebral microcirculation, the animal mesenteric microcirculation, the bulbar conjunctiva microcirculation and the fundus retinal microcirculation), the distance from the tip of the probe device to the probe sleeve on the host body can be adjusted, so that the instrument can allow observation through air. However, the existing similar instruments can only allow observation when closely touching the observed object and cannot realize observation through air, so the range of application is narrow.

Finally, it is to be noted that, the inventor(s) firstly discover the theory of the high-speed blood flow intensity, spreading rate and duration and the acceleration or deceleration of the infectious shock (septic shock), and then invent the microcirculation shock monitor enabling rapid and repeated positioning, the monitoring system and the monitoring method by monitoring the four specific indicators according to the theoretical discovery.

If the theoretical discovery and four indicators and the acquisition method thereof are not proposed, there is no requirement of developing the rapid and repeatable positioning function, and the zooming mechanism of a zoom microscope will not be used to expand the search range for repeated positioning and observation. For the above two reasons, this is not an obvious invention.

It is difficult to discover the pathogenic mechanism of a disease. Even with the discovery of the mechanism, unless indicators are also discovered and proposed according to the mechanism, it is still impossible to invent the instrument. This is like the case that it is difficult to discover and create a potential human need, and it is also difficult to invent the desired product.

For example, as to some technologies, for example, pattern-type Window 3.1 is created by Microsoft Corp. early by integrating commands of the DOS operating system, such that those who do not understand DOS commands also could use computers. As for the technology per se, it seems to be obvious because the system software engineers can integrate the commands, but it is a great creation to discover the potential need of ordinary people and then make the creation to satisfy the need.

For another example, it seems to be technically obvious that a mobile phone becomes a smartphone by using a simplified computer operating system in the mobile phone. However, the smartphone is certainly an amazing invention because of the discovery and creation of the universal demands.

Since the theory of the above-mentioned high-speed blood flow intensity and duration and the acceleration and deceleration change of the sublingual microcirculation of the early and middle stage infectious shock (septic shock) proposed by the inventors has yet not been publicly issued, no articles about the same are issued in China and abroad, let alone consensus in the intensive care medicine in China and abroad. Meanwhile, the four indices of the early and middle stages of infectious shock (septic shock) proposed by the inventors according to the theory of the high-speed blood flow intensity and duration and the acceleration and deceleration change and the acquisition methods thereof are still not publicly issued at present, and there are still no issued papers about diagnosis of septic shock according to the four indices in China and abroad. In the current intensive care medicine, the four indices have yet not been used as specific indices of infectious shock, that is to say, doctors in the intensive care medicine are unable to use the four indices measured by the inventors to diagnose the infectious shock (septic shock) according to the current knowledge. Therefore, currently, the four indices proposed by the inventors are only a method for acquiring and monitoring parameters, rather than a method for diagnosing diseases. See Documents 6 and 7.

BRIEF DESCRIPTION OF THE DRAWINGS

The present invention is further described below according to the accompanying drawings and embodiments.

In the figures.

Figure 1:
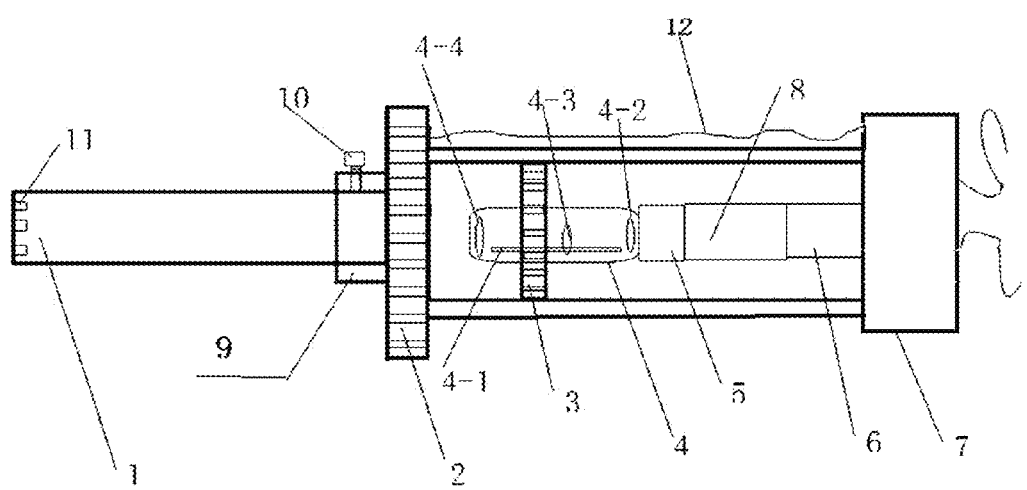
FIG. 1 is a structural diagram of a microcirculation shock monitor enabling rapid and repeated positioning according to the present invention.

1. probe device, 2. focusing tube, 3. zooming knob, 4. microscope continuous zooming mechanism, 4-1. zooming mechanism driving and guiding device, 4-2. rear lens, 4-3. zooming lens, 4-4. front lens, 5. direction adjustment mechanism, 6. cross calibration mechanism, 7. camera, 8. parfocalization mechanism, 9. probe sleeve, 10. adjustment and positioning mechanism, 11. illumination source, 12. anode-cathode lead, 13. handle, 14. disposable sterile sheath, 15. host body, 16. axial movement direction, 17. external power source and video line, S. actual length of the probe device, S1. exposed length of the probe device in normal close observation, S2. exposed length of the probe device in air observation, L. imaging distance, W. air distance.

DETAILED DESCRIPTION OF EMBODIMENTS

The present invention is further described below in combination with embodiments.

As shown in FIG. 1 and FIG. 2-FIG. 5, a microcirculation shock monitor enabling rapid and repeated positioning includes a host body 15, wherein the host body 15 is cylindrical, a probe device 1 is mounted at a front end of the host body 15, the probe device 1 is an elongated tube, an illumination source 11 is provided at an end portion of the probe device, wherein the illumination source 11 can be an LED light source provided inside the front end of the probe device, an anode-cathode lead 12 of the illumination source is connected to a power source at a position of a camera, the lead 12 of the illumination source can be mounted inside a lead tube or directly extended out from the host body 15 and connected to the power source at the position of the camera, such that a main structure is compact; the illumination source also can obtain power from the outside through a coaxial light source. A handle 13 can be additionally provided in a lower portion of the microcirculation shock monitor enabling rapid and repeated positioning of the present invention, so that it is convenient for holding and controlling a viewing angle. A disposable sterile sheath 14 is on the probe device 1, which sheath functions to keep an observed surface flat and prevent cross infection.

A microscope continuous zooming mechanism 4 is mounted in the host body 15, and a zooming knob 3 is mounted outside the host body 15. A rear lens 4-2 of the microscope continuous zooming mechanism 4 is directly connected behind to a camera 7 through a direction adjustment mechanism 5 and/or a parfocalization mechanism 8 and/or a cross calibration mechanism 6. At least one zooming lens 4-3 capable of reciprocating along a direction of a zooming mechanism driving and guiding device 4-1 is provided between a front lens 4-1 and the rear lens 4-2 of the microscope continuous zooming mechanism 4. The microscope continuous zooming mechanism 4 can have a structure shown in FIG. 1: two ends of the microscope continuous zooming mechanism 4 are respectively mounted with the front lens 4-4 and the rear lens 4-2, the zooming mechanism driving and guiding device 4-1 is provided inside the microscope continuous zooming mechanism 4, and a zooming lens 4-3 capable of reciprocating in an axial movement direction 16 is mounted on the zooming mechanism driving and guiding device 4-1. The zooming lens 4-3 functions to continuously zoom in the reciprocating motion so as to realize the function of quickly and repeatedly positioning an observed area. The camera 7 can be a CCD camera.

After the microscope continuous zooming mechanism is mounted, the range of field of view can be calculated according to a formula for a range of field of view of an industrial lens: a size of field of view=(a size of CCD format)/(an optical magnification power). When the optical magnification power is 0.9× and CCD1/3" is 3.6 mm in length and 4.8 mm in width, the size of the field of view is 3.6/0.9=4 mm in length and 4.8/0.9=5.33 mm in width, and the range of the field of view is 4×5.33=21.32 square millimeters.

When the optical magnification power is 4.5× and CCD1/3" is 3.6 mm in length and 4.8 mm in width, the size of the field of view is 3.6/4.5=0.8 mm in length and 4.8/4.5=1.06 mm in width, and the range of the field of view is 0.8×1.06=0.848 square millimeters.

When a magnification power of an objective lens is 4.5× (a target area of the CCD camera is 1/3), the field of view becomes smaller, and the range of the field of view is 1.06×0.8=0.848 square millimeters; and when the magnification power of the objective lens is 0.9×, the field of view becomes larger, and the range of the field of view is 5.33×4.0=21.32 square millimeters. Therefore, when the range of the field of view changes from 4.5× to 0.9×, the microscopic search range is increased by 25.15×, ensuring that an original blood vessel is found quickly.

In comparison, the field of view of a 5× lens abroad is 0.94×0.75=0.705 square millimeters, then 21.33/0.705=30, i.e., the range of the field of view in the present invention is 30 times of that abroad (referring to page 5 of Document 5: The optical field of view of SDF imaging with 5× objectives is approximately 0.94 mm×0.75 mm).

A focusing tube 2 is mounted in a rear portion of the probe device 1 or on the front lens 4-4 of the microscope continuous zooming mechanism 4 or on the camera 7. The focusing tube 2 enables the elongated tubular probe device 1 or the front lens 4-4 of the microscope continuous zooming mechanism or the CCD camera 7 to reciprocate along the axial movement direction 16, so as to realize fine tuning of image definition.

A direction adjustment mechanism 5 and/or a parfocalization mechanism 8 and/or a cross calibration mechanism 6 is mounted between the microscope continuous zooming mechanism 4 and the camera 7, wherein the direction adjustment mechanism 5 ensures that an image will not be rotated arbitrarily in 360-degree orientation, the parfocalization mechanism 8 ensures that the image remains in a clear state in the case of a minimum magnification power or a maximum magnification power of the instrument, and the cross calibration mechanism 6 ensures that a center of the image remains unchanged in zoom-out and zoom-in processes. All these mechanisms are designed to further ensure and optimize the repeated positioning and observation.

Figure 3:
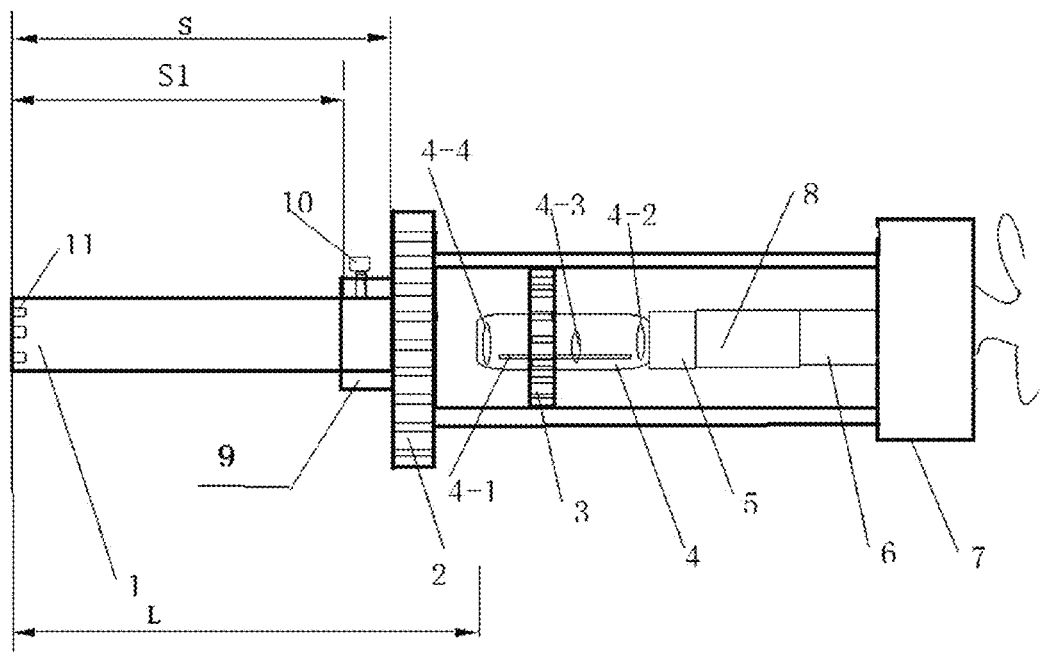
FIG. 3 is a schematic diagram of a positional and structural relationship between a probe device and a microscope continuous zooming mechanism when the present invention is normally pressed against an observed object for observation.
Figure 4:
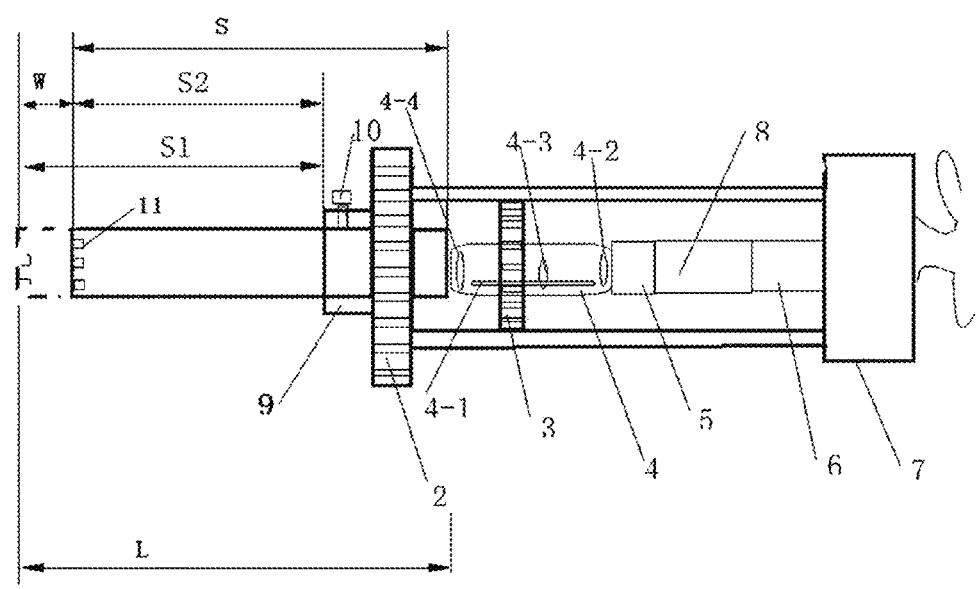
FIG. 4 is a schematic diagram of an air distance generated by an axial movement of the probe device relative to a host body according to the present invention.
Figure 5:
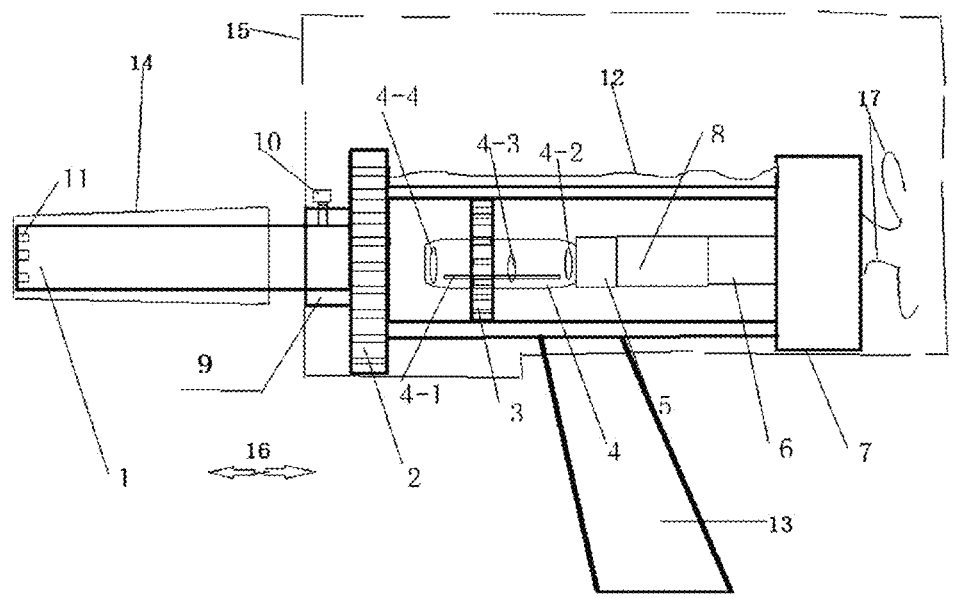
FIG. 5 is a schematic diagram of an embodiment of the present invention with a handle.
Figure 6:
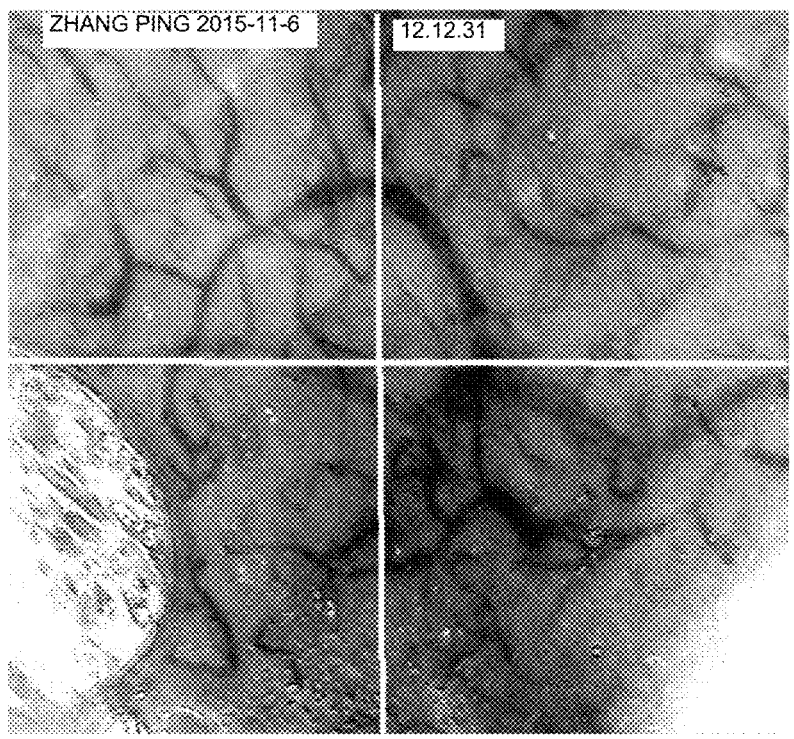
FIG. 6-FIG. 8 are images of the same blood vessel of the same person at a certain moment before and after magnification.
Figure 7:
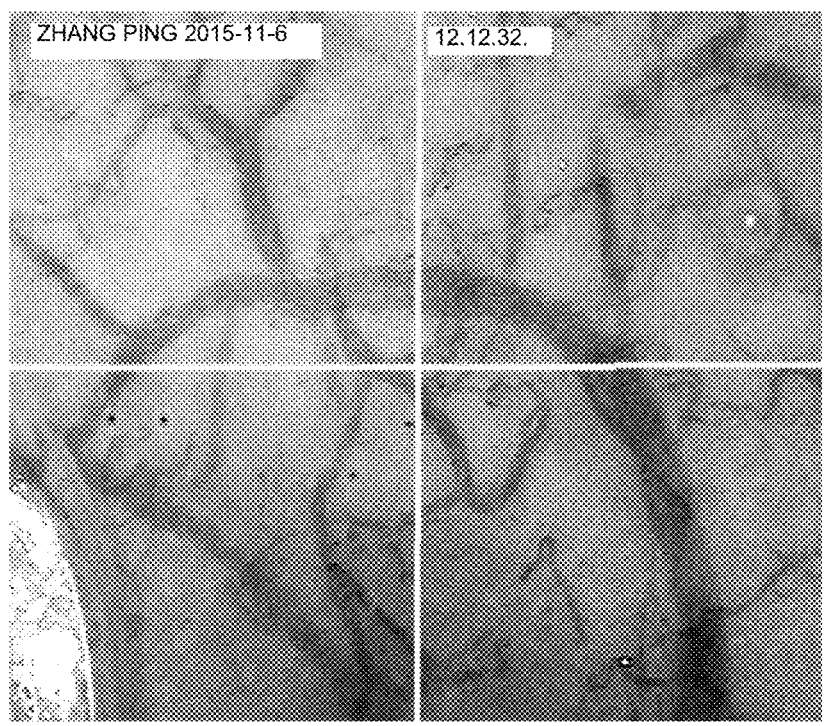
Figure 8:
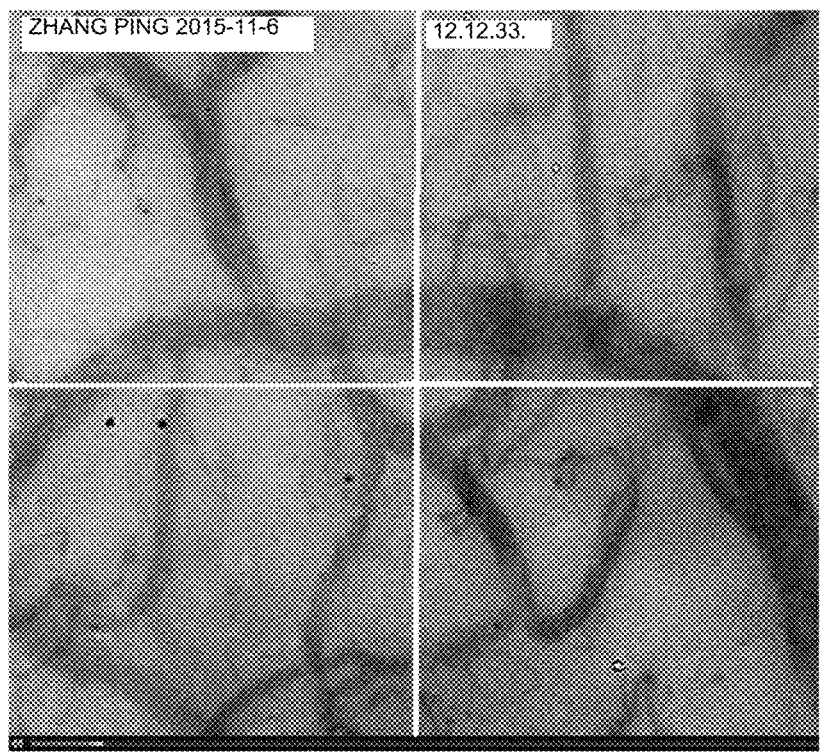
Figure 9:
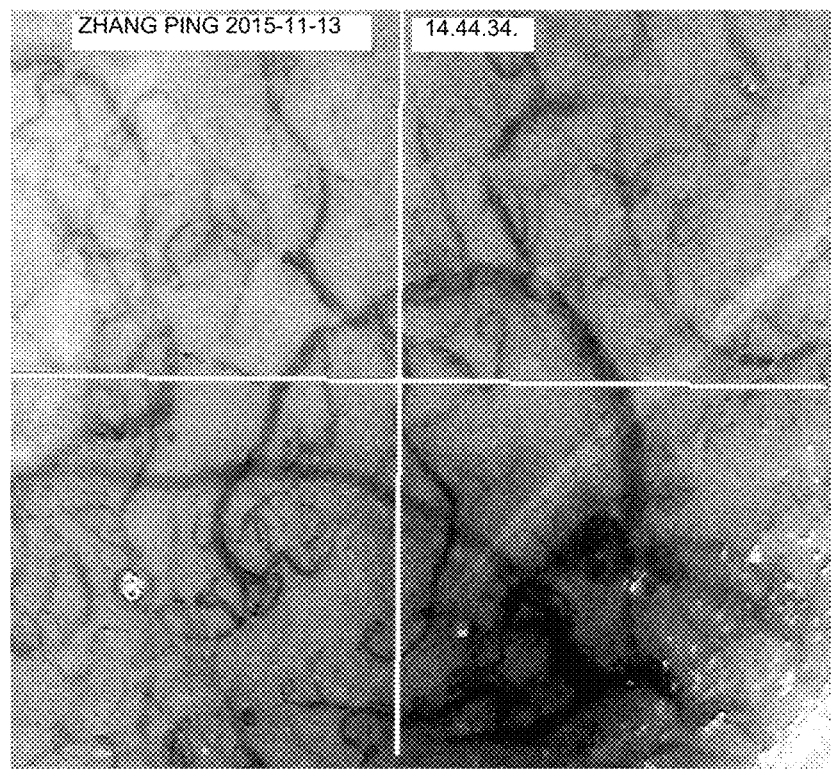
FIG. 9-FIG. 10 are images of a same blood vessel of the same person at another moment before and after magnification.
Figure 10:
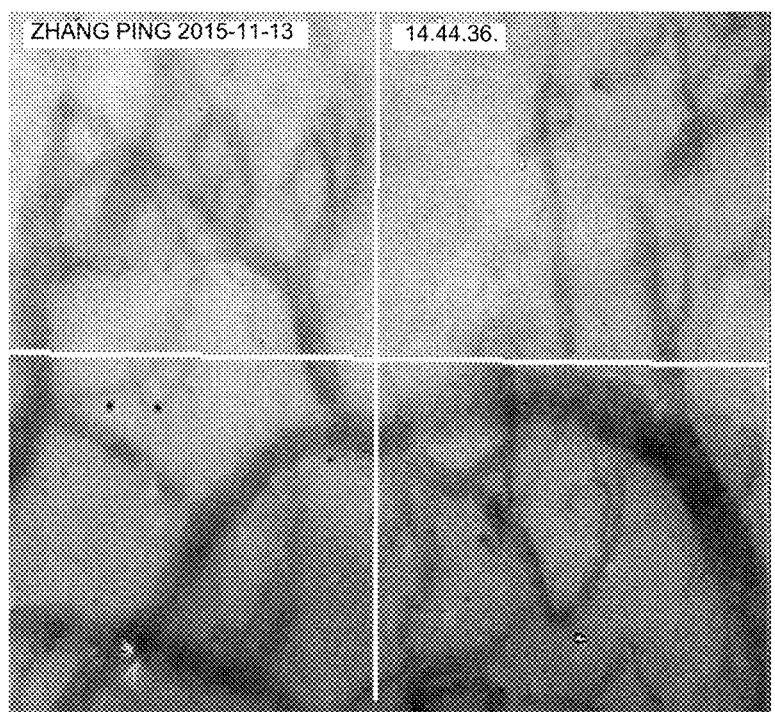

As shown in FIG. 3 and FIG. 4, the probe device 1 is connected by a probe sleeve 9 in such a way that the probe device 1 can move axially relative to the host body 15 along the axial movement direction 16. An adjustment and positioning device 10 is mounted between the host body 15 and the probe device 1. When the adjustment and positioning device 10 is loosened, the probe device 1 can move back and forth relative to the host body along the axial movement direction 16. When the adjustment and positioning device 10 is locked, the probe device 1 is fixed again. In the case of the normal close observation (FIG. 3), an actual length S of the probe device is equal to an imaging distance L, and an air distance W is equal to 0.

When the probe device cannot be directly pressed against a target for observation (FIG. 4), the adjustment and positioning device 10 is loosened, and the probe device 1 can move backward relative to the host body 15 along the axial movement direction, and then, the adjustment and positioning device 10 is locked, and the probe device 1 is fixed again. At this, an exposed length S2 of the probe device in the air observation is less than the exposed length S1 of the probe device in the normal close observation, and the air distance W is greater than 0. As the imaging distance L is unchanged, the air observation can be realized (e.g., at positions where only air observation can be carried out, for example, rat craniocerebral microcirculation, animal mesenteric microcirculation, bulbar conjunctiva microcirculation and fundus retinal microcirculation).

The microcirculation shock monitor enabling rapid and repeated positioning of the present invention is used in the following way: firstly, a patient is kept to lie on the back as specified, the probe device 1 and the disposable sterile sheath 14 are preliminarily aligned with a roughly specified position of the sublingual mucosa of the patient, then one large blood vessel and several neighboring blood vessels which are easy to observe are found by rotating the zooming knob 3 within a large low-magnification field of view, where the blood vessels can be named or numbered, and the blood vessels are locked in a center of a screen by a crosshair in an image acquisition window on a computer screen, then the zooming knob 3 is adjusted, and the blood vessels are gradually magnified to the maximum such that blood flow in capillaries can be observed clearly (it takes only 2 to 3 seconds). The parfocalization mechanism 8 ensures that the image remains in a clear state in the case of a minimum magnification power and a maximum magnification power of a detector, and the cross-calibration mechanism 6 ensures that the center of the image remains unchanged in the zoom-out and zoom-in processes. Finally, millimeter-scale fine tuning is performed by the focusing tube 2 to obtain the clearest images, and the images are stored in a computer hard disk of the monitoring system of the present invention.

The above steps are repeated during the acquisition within the second period of time, and after a rough area is seen, the probe device 1 is moved slightly and finely turned all around to observe an image of the same blood vessel in the same area, and the image is locked, recorded and stored in the monitoring system of the present invention for accurate comparison and analysis.

When a blood flow rate and distribution of large blood vessels and surrounding capillaries thereof are observed at a high magnification power, the large blood vessels and surrounding capillaries thereof can be named or numbered again for easy identification and positioning. The images acquired this time can be transmitted to and stored in the monitoring system of the present invention. By the monitor of the present invention, the microscopic field of view can be expanded from less than one square millimeter to about 25 square millimeters. By using a large field of view at a low magnification power, it is convenient for repeated positioning, so that a previously observed part can be found within a large range. After the previously positioned large blood vessels are found, this position is locked in a video acquisition window of the computer screen (the crosshair in the center of the video window is more convenient for locking), then the magnification power is adjusted, such that the image is gradually magnified at the original position, and the effect that the position is unchanged while the magnification power is increased so that the same capillaries previously numbered surrounding the large blood vessel is achieved. The parfocalization mechanism can magnify the image while keep the definition unchanged, thus it is convenient to observe changes in blood flow rate of the same capillaries surrounding the large blood vessel. The image acquired this time can be transmitted to and stored in the monitoring system of the present invention. Although the elongated probe device 1 is randomly inserted in or taken out from roughly the same observed part, the previously observed large vessel still can be quickly found within 2-3 seconds by searching within the large field of view at a low magnification power. By comparing the previous and last images, changes in the blood flow rate and the distribution at the same observed position can be obtained accurately. For related observed effects, refer to FIG. 6-FIG. 10.

Embodiments of the microcirculation monitoring system:

In the research process, the inventors have found high-speed blood flow intensity, spreading rate and duration and changes of acceleration and deceleration of the sublingual microcirculation of patients with early and middle stage infectious shock (septic shock), and meanwhile have guided experiment personnel in animal experiments to successfully monitor repeatedly and continuously the induction of high-speed blood flow of the same blood vessel in the sublingual microcirculation of animals (intravenous injection of lipopolysaccharide LPS). Then, the inventors provide the following theoretical descriptions for the above phenomenon:

Firstly, the high-speed blood flow defined herein is a high-speed blood flow appearing in capillaries in the sublingual mucosal microcirculation. The average blood flow rate in capillaries of a healthy person is 600 μm/s±450, and is up to 1200 μm/s (children and the elderly will be different). However, it is found that the flow rate of the high-speed blood flow is generally greater than 1500 μm/s. The selected range of blood vessels is different from that in the international round table conference in 2007 (Document 5). In Document 5, the TVD, PVD, PPV, MFI and other indices of capillaries within a diameter less than 20 μm are observed.

Herein in the observation, it is required to average the flow rates of two fastest blood vessels within the microscopic field of view (it is possible to select the fastest blood vessel upon comparison of 3-5 observation points). Generally, the thickness of the blood vessels is taken into consideration. However, it is preferred to select blood vessels greater than 20-25 μm in diameter because the flow rate in the large blood vessels is relatively stable and difficult to disappear. In the case where large and small blood vessels roughly have the same highest blood flow rate, the largest blood vessel is preferred as a sample for calculating the blood flow rate. In the observation, it is to be noted that it is best to select no less than two such blood vessels with the highest blood flow rate within the field of view and an average blood flow rate thereof is taken. If there is only one blood vessel with the highest blood flow rate, the flow rate of this blood vessel is taken as the average.

The fact that the high-speed blood flow appears in the early and middle stages of infectious shock (septic shock) is based on the following findings and research:

It is well-known that, the microcirculations of a dying person are definitely in a stagnated state—it will stop after death. This situation has also been verified by experiments on animals. Thus, reversely, the high-speed blood flow intensity must appear in the early and middle stages of diseases. This logical deduction is made by a method of exclusion.

In a sublingual microcirculation experiment on animals, after 15 minutes of intravenous injection of lipopolysaccharide (LPS), the blood flow begins to accelerate. This experiment highly supports the above conclusion obtained by the logical deduction.

The high output and low resistance appearing in the early stage of shock in the shock theory is actually the phenomenon of high-speed blood flow intensity. This also proves that the high-speed blood flow intensity occurs in the early and middle stages of infectious shock.

Mechanism of generation of high-speed blood flow or inevitability of generation of high-speed blood flow:

The generation of the high-speed blood flow is a reflection of self-protection of the body. When there is a lot of toxin in the blood of the body and it is difficult to deactivate the toxin only by the blood, the blood flow will be accelerated to quickly transport the toxin to organs such as the liver, lung and kidney for detoxification and deactivation. It is indicated that the occurrence of the high-speed blood flow is a manifestation in the early and middle stages of infectious shock (septic shock), and it also shows the cause, mechanism and inevitability of the high-speed blood flow. For example, in times of peace, people keep the normal working rhythm, but if there are emergencies such as disasters and wars, an emergency mechanism will be adopted, in this case, the working rhythm of organizations and human beings will be quickened so as to cope with the emergencies. For another example, it is also an emergency mechanism to establish green channels in hospitals to save patients with cardiovascular and cerebrovascular diseases. The occurrence of the high-speed blood flow is theoretically similar to the emergency mechanism in the peaceful society and the green channels in hospitals. Therefore, the discovery of the high-speed blood flow indicates that there is a very large amount of toxin in the body so that the emergency mechanism is activated in the body, and also that it is still in the early stage of the disease. In the future, the infection can even be classified into high-speed blood flow intensity infection and non-high-speed blood flow intensity infection (high intensity infection and no-high intensity infection, for short) so as to distinguish the strength of the toxin and the severity of the infection. The high-speed blood flow disrupts the normal rhythm of exchange of nutrients and oxygen in the microcirculation, so that the organs and cells are in a long-standing sharply hypoxic state, thereby resulting in septic shock. This is the primary cause of sepsis.

For general inflammations, detoxification can be realized by the blood itself as the strength of toxin in the blood is low, then the high-speed blood flow will not be activated in the body to quickly convey the toxin to the liver for detoxification. It is assumed that if the high-speed blood flow also occurs in the general inflammations, such high-speed blood flow inevitably will disrupt the normal rhythm of the exchange of nutrients and oxygen in the pulse blood, so that the organs and cells will be continuously starved of oxygen, thereby finally leading to the septic shock inevitably. However, as is known, the general infections, for example, cold or general pneumonia, will not show any shock symptom. This proves the above conclusion.

The high-speed blood flow will not occur in the general inflammations, and will only occur in the severely inflected sepsis. This finding has clinically provided specific indices for the detection of the early sepsis, i.e., the high-speed blood flow intensity ratio, the high-speed blood flow similarity, the high-speed blood flow intensity duration and the difference of abnormal high-speed blood flow intensity change proposed herein.

The high-speed blood flow intensity is not invariable. In the early stage of the infectious shock, the high-speed blood flow is accelerated gradually; in the middle stage of the infectious shock, the high-speed blood strength substantially can remain unchanged; in the middle and advanced stage, the high-speed blood flow intensity begins to decrease and weaken; and in the advanced stage of the infectious shock, there is substantially no high-speed blood flow. Of course, if the rescue is timely and effective, the high-speed blood flow intensity also will gradually return to the normal blood flow state—which should be comprehensively determined with reference to other indices. The authors of Document 5 and Document 9 exactly ignore this point, and therefore deny the presence of the high-speed blood flow.

Impetus for the generation of the high-speed blood flow:

The high-speed blood flow intensity is formed under the combined effect of the cardiac output with the capillary sphincter and smooth muscle. The high output and low resistance in the shock theory is actually theoretical explanation of the phenomenon of the high-speed blood flow intensity. Macroscopically speaking, the high output therein is the increase of the cardiac output; and microscopically speaking, the low resistance is formed by sphincter and smooth muscle that directly promote the blood flow in capillaries. The acceleration of the rhythmic frequency and the increase of the contraction intensity of the sphincter and smooth muscle rise the blood pressure and quicken the blood flow in the capillaries, so that the low resistance phenomenon occurs synthetically. Since the microcirculation is generally referred to as a second heart, the microcirculation has its own ability to regulate the blood flow in the microcirculation, and the impetus for directly promoting the blood flow in the capillaries is provided by the sphincter and smooth muscle, the occurrence of the phenomenon of the high output and low resistance is caused by the combined effect of the heart with the capillary sphincter and smooth muscle—which are two direct impetuses for the generation of the high-speed blood flow.

Relationship between the high-speed blood flow and the infectious shock:

From the above theoretical deduction, it can be known that the continuous high-speed blood flow intensity causes fatigue, cramp, pseudoparalysis or even complete paralysis of the sphincter and smooth muscle, and eventually damages the blood flow regulation mechanism of the capillaries, resulting in ineffective opening of lots of true capillaries, and sudden insufficient effective blood volume, and leading to the shock caused by the sudden drop in blood pressure.

Although this deduction is very simple, it is a very important conclusion because it indicates the direct cause of the infectious shock.

G. What toxin can result in the high-speed flood flow?

The toxin is strong as long as the toxin can finally result in the infectious shock, regardless of the type of the toxin. In the early stage, the high-speed blood flow intensity will be generated. The process of quickly conveying the toxin to the liver for detoxification is the high-speed blood flow intensity phenomenon. In the middle and advanced stages, the high-speed blood flow intensity will continue. In the advanced stage, the high-speed blood flow intensity will result in the paralysis of capillary sphincter and smooth muscle and eventually cause shock. Therefore, it is found that the high-speed blood flow intensity and the duration thereof indicate that the toxin in the body is relatively strong, and it can be known that the infectious shock is about to happen or has already happened. As for the type of the toxin, i.e., toxic dysentery, encephalitis, sepsis or hemorrhagic fever, it needs to be determined in combination with other indices. However, regardless of the type of the toxin, the occurrence of the high-speed blood flow intensity and the duration thereof are signs of relatively strong toxin in the blood and precursors of possible attack of the infectious shock. Hence, endotoxins or exotoxins will induce the high-speed blood flow if they are toxic enough. Common influenza viruses with low toxicity will not induce the high-speed blood flow.

H. Specificities of the blood flow rate in the sublingual microcirculation of a patient with infectious shock different from that of a healthy person in four aspects are summarized:

I. Under the premise that the patient suffers from inflection and organ injury, in the sublingual mucosal microcirculation of the patient with infectious shock of the early and middle stages, there will be a blood flow whose highest blood flow rate is far greater than the highest blood flow rate in the sublingual mucosal microcirculation of a healthy person, and this blood flow is also referred to as high-speed blood flow for short. The average blood flow rate in the sublingual mucosal microcirculation of a healthy person is generally 600 μm, and a normal value of the average highest blood flow rate thereof is 1200 μm/s. However, the blood flow rate obtained from sampling test of the sublingual mucosal microcirculation of the patient with sepsis is about 2000 μm to 3000 μm. Therefore, the highest blood flow rate in the sublingual mucosal microcirculation of the patient with early and middle stage infectious shock will be accelerated to at least no less than 1.5 times of the average highest blood flow rate of the healthy person. This is a first specificity for distinguishing the blood flow in the sublingual mucosal microcirculation of the patient with infectious shock from the blood flow in the sublingual mucosal microcirculation of the healthy person, i.e., high-speed blood flow specificity.

2. Ratio of a length of all blood vessels with the high blood flow rate to the total length of all capillaries within the field of view (similitude): the bigger the ratio is, the more complete the high-speed blood flow of the infectious shock is activated, and a smaller ratio reflects that the high-speed blood flow is in an activated state or a vanishing state. This is a second specificity for distinguishing the blood flow in the sublingual mucosal microcirculation of the patient with infectious shock from the blood flow in the sublingual mucosal microcirculation of the healthy person.

3. Such high-speed blood flow will last for at least no less than four hours, and this situation does not exist for a healthy person. Therefore, this is a third specificity. The longer the duration is, the sooner the onset of the infectious shock is.

4. A fourth specificity is that the high-speed blood flow will be gradually accelerated in the early stage, will maintain the high speed in the middle stage, and will gradually slow down in the middle and advanced stages. However, the microcirculation speed of a healthy person is constant, without such acceleration that is varied greatly. This is the fourth specificity for distinguishing the blood flow in the sublingual mucosal microcirculation of the patient with infectious shock from the blood flow in the sublingual mucosal microcirculation of the healthy person (The sublingual microcirculation of the healthy person also has periodical speed changes within 24 hours per day, but such speed changes are in a small range).

I) Based on the above theoretical findings, since the sublingual microcirculation speed of the healthy person is constant in the same blood vessel, with the average speed of 600 μm/s, while the normal value of the average highest blood flow rate of the healthy person is 1000 μm/s, the high-speed blood flow intensity (greater than 1500 μm/s), spreading rate and duration in the same blood vessel and the acceleration and deceleration changes thereof will not occur for the healthy person. Therefore, they can be used as the specific indices of the early and middle stages of the infectious shock. Hence, the inventors propose the four specific indices and methods for acquiring the same.

A method for acquiring the first one of the four specific indices is as follows:

The high-speed blood flow intensity ratio refers to a ratio of an average highest blood flow rate in the sublingual microcirculation of the patient of infectious shock within the field of view to an average highest rate in the sublingual microcirculation of the healthy person.

The high-speed blood flow intensity ratio R is: $R=P/N*100\%$.

P is the average of highest blood flow rates in the sublingual microcirculation of the patient with infectious shock within the field of view (prestissimo).

N is the average of highest blood flow rates in the sublingual microcirculation of the healthy person (normal).

This index mainly evaluates the high-speed blood flow intensity.

A method for acquiring the second one of the four specific indices is as follows:

The high-speed blood flow spreading rate refers to a ratio of a total length of all blood vessels with the high blood flow rate to a total length of all capillaries within the field of view.

The high-speed blood flow spreading rate S is: $S=HL/TL*100\%$.

HL is the total length of all blood vessels with the high-speed blood flow rate within the field of view.

TL is the total length of all blood vessels within the same field of view.

This index mainly evaluates whether the high-speed blood flow is activated relatively completely.

A method for acquiring the third one of the four specific indices is as follows:

The high-speed blood flow intensity duration (Time) refers to a time interval between a time when the high-speed blood flow is found for the first time and a time when the high-speed blood flow begins to decelerate.

The high-speed blood flow intensity duration T is $T=T2-T1$ (with respect to the same blood vessel within the same field of view), where T is the high-speed blood flow intensity duration, and T1 is the time when the high-speed blood flow is found for the first time, and it also can be traced and determined according to other manifestations of the patient (for example, the initial onset time or the like).

T2 is the time when the high-speed blood flow begins to decelerate.

This index mainly traces the possible historical time of occurrence of the high-speed blood flow and judge the possible approaching time of the infectious shock.

A method for acquiring the fourth one of the four specific indices is as follows:

The difference of abnormal high-speed blood flow intensity change which refers to the acceleration change of the high-speed blood flow in the sublingual microcirculation of a patient with infectious shock in previous and later periods of time, i.e., abnormal acceleration or abnormal deceleration of the high-speed blood flow in the sublingual microcirculation of the patient with infectious shock within different previous and later periods of time.

The difference of abnormal high-speed blood flow intensity change D is: D=D1−D2.

D is a difference of abnormal change in high-speed blood flow intensity of the patient with infectious shock, D1 is a difference of changes in highest blood flow rate of the patient with infectious shock, D2 is a difference of highest blood flow rate change of the healthy person.

The difference of highest blood flow rate change of the patient with infectious shock D is: D1=P2−P1

P2 is an average of last measured highest blood flow rates of the patient with infectious shock.

P1 is an average of previously measured highest blood flow rates of the patient with infectious shock measured previously.

If D1 is greater than 0, it means that the blood flow rate is accelerated; if D1 is less than 0, it means that the blood flow rate is decelerated; if D1 is equal to 0, it means that the blood flow rate is stable.

$$D2=P4-P3.$$

D2 is a difference of changes in highest blood flow rate of the healthy person.

P4 is an average of last measured highest blood flow rates of the healthy person.

P3 is an average of previously measured highest blood flow rates of the healthy person.

(This numerical value is generally equal to 0, that is to say, the sublingual blood flow of a healthy person is generally in a constant flow state when the person does not do strenuous exercise).

Since the sublingual blood flow of a healthy person is generally in the constant flow state when the person does not do strenuous exercise, actually, the difference D of the abnormal changes in blood flow rate of the patient with infectious shock is equal to the difference D1 of changes in highest blood flow rates of the patient with infectious shock, that is, D=D1.

The formula is simplified as follows: D=D1=P2−P1, i.e., a difference between averages of the last and previous high-speed blood flow rates in the same blood vessel in the sublingual circulation of the patient with infectious shock.

If D and D1 are greater than 0, it means that the blood flow rate is accelerated; if D and D1 are less than 0, it means that the blood flow rate is decelerated; if D and D1 are equal to 0, it means that the flow rate is stable.

Since the blood flow rate of a healthy person is stable, P4-P3 is equal to 0, then the difference of abnormal changes in high-speed blood flow intensity of a monitored object is D=D1−D2=D1=P2−P1, that is, equal to a difference between the average P2 of last measured highest blood flow rates of the patient with infectious shock and the average P1 of previously measured highest blood flow rates of the patient with infectious shock.

This index is mainly used to judge presence of the high-speed blood flow and different stages of the infectious shock. Since the blood flow of a healthy person is generally in a constant flow state when the person does not do strenuous exercise, the abnormal acceleration and abnormal deceleration of the blood flow rate will not occur to a healthy person. The occurrence of such situation (the abnormal acceleration and abnormal deceleration), even if the blood flow rate is not very high, is the fourth specific index of the infectious shock. The abnormal acceleration of the flow rate reflects an activation stage of the high-speed blood flow of the early stage of the infectious shock, and the abnormal deceleration of the flow rate reflects that the infectious shock is at the middle and advanced stages.

The above methods for acquiring the four specificity indices depend on that the instrument must have a function of being capable of continuously observing the same blood vessel and blood vessels in the microcirculation of the same area within different periods of time (also referred to as a function of being capable of positioning repeatedly for short).

A microcirculation shock monitoring system is provided, which includes data acquisition modules, a data preprocessing module, a comparison module and a storage module.

The data acquisition module is configured to repeatedly position and observe same blood vessels in the same monitored area in different periods of time and acquire blood vessel image data, wherein the data acquisition module includes a healthy person data acquisition module and a patient data acquisition module, being respectively provided in different databases; a crosshair locking function is provided in an acquisition window; the acquisition modules have a photographing and video recording module, with an additional function of comparing pictures and videos, and besides conventional parameters, an acquisition time, an acquisition object, a name, age, gender and other necessary information are displayed on acquired pictures and videos.

In order to accurately acquire data of blood vessels at the same part within a previous period of time and a later period of time, the acquisition module has a function of simultaneously displaying the previously acquired images, and a collector can meanwhile consult the previously acquired videos and pictures for on-site data acquisition.

A crosshair is on the acquisition window and the acquired video for positioning, with the acquisition time—year, month, day, hour, minute and second, the name of the acquired object and other necessary information.

The data preprocessing module is configured to filter and stabilize the acquired blood vessel image data, for example, image stabilization and cropping: stabilizing a jitter image upon treatment such that the image does not jitter to facilitate analysis, and an unanalyzable part jittering too much is removed; calculation of a sample value: locally collecting samples of highest blood flow rates of sublingual microcirculations of healthy persons for different ages, genders, races and occupations at different periods of time and then statistically analyzing the same to obtain a range of normal value; observing a difference of changes over time in the highest blood flow rate in the sublingual microcirculations of healthy persons to obtain a range of normal value.

The comparison module is configured to compare measured stabilized blood vessel image data with reference data, to judge and analyze changes in the flow rate in the blood vessel and/or changes in density.

The storage module is configured to store the measured blood vessel image data and the reference data in a database.

Figure 2:
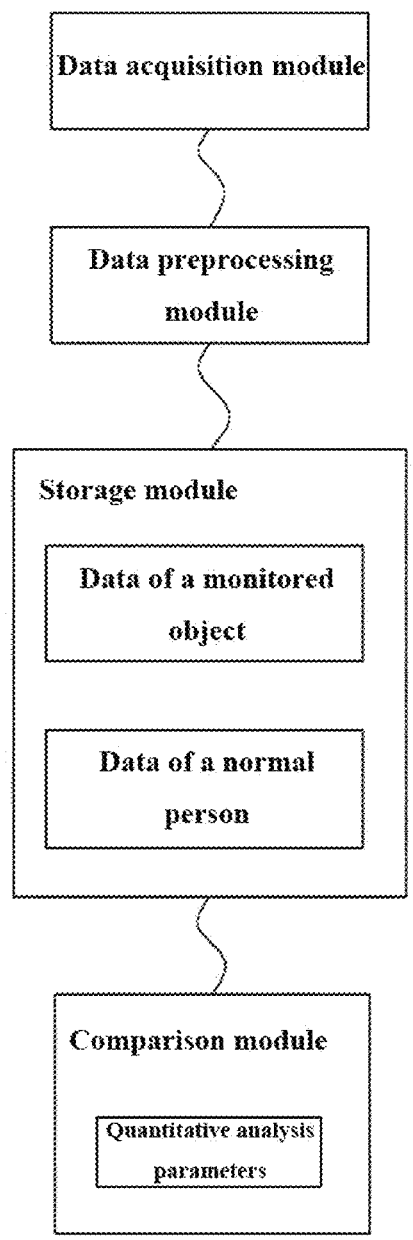
FIG. 2 is a flowchart of a microcirculation shock monitoring system according to the present invention.

As shown in FIG. 2, the microcirculation shock monitoring system is further improved.

The data preprocessing module includes a blood flow rate measurement module, configured to generate real-time flow rate data in the blood vessel;

data stored in the storage module includes real-time data and historical data of the blood vessel images of a monitored object, average data of highest microcirculation blood flow rates of a healthy person, difference data of changes in blood flow rates of a healthy person, and stabilized data of the above data; and in the comparison module (data having been stabilized), there are quantitative analysis parameters.

The four specific parameters are specifically described as follows.

The quantitative analysis parameters include a high-speed blood flow intensity ratio R.

This parameter is mainly used to evaluate the strength of the high-speed blood flow.

The high-speed blood flow intensity ratio R refers to a ratio of an average of highest blood flow rates in the sublingual microcirculation of a patient with infectious shock within the field of view to an average of highest blood flow rates in a sublingual microcirculation of a healthy person.

The high-speed blood flow intensity ratio is $R=P/N*100\%$,

R is the high-speed blood flow intensity ratio.

P is the average of highest blood flow rates in the sublingual microcirculation of the patient with infectious shock within the field of view (prestissimo).

N is the average of highest blood flow rates in the sublingual microcirculation of the healthy person (normal).

The greater this ratio is, the higher the high-speed blood flow intensity is, and the higher the blood flow rate is. The occurrence of the high-speed blood flow intensity indicates that the toxin is highly toxic and is difficult to be deactivated by the blood itself, so that the brain activates the high-speed blood flow to quickly convey the toxin to the liver for detoxification. The occurrence of the high-speed blood flow indicates possible development of infectious shock (sepsis).

The quantitative analysis parameters include the high-speed blood flow spreading rate.

This parameter is mainly used to evaluate whether the high-speed blood flow is activated completely.

The high-speed blood flow spreading rate is a ratio of a total length of all blood vessels at a high blood flow rate to a total length of all capillaries within the field of view.

The high-speed blood flow spreading rate is $S=HL/TL*100\%$,

S is the high-speed blood flow similarity

HL is the total length of all blood vessels at a high speed blood flow rate within the field of view TL=the total length of all blood vessels within the same field of view (In order to simplify the calculation, the microcirculation blood flow rate is classified according to the classification method in the international round table conference in 2007: retention=1, intermittent flow=1, slow flow=2, continuous flow=3, and high-speed flow=4.)

Example 1 if the total length of all blood vessels within the field of view is 6000 μm and the blood flow in all capillaries is high-speed blood flow, then the total length of the high-speed blood flow is also 6000 μm, then spreading rate $(S)=6000/6000=1*100\%=100\%$, which indicates complete similitude.

Example 2 if the total length of all blood vessels within the field of view is 8600 μm and the total length of the high-speed blood flow therein is 4300 μm, then spreading rate $(S)=4300/8600=0.5*100\%=50\%$, which indicates semi-similitude.

Example 3 if the total length of all blood vessels within the field of view is 10000 μm and the total length of the high-speed blood flow therein is 100 μm, then spreading rate $(S)=100/10000=0.01*100\%=1\%$, which indicates that there is nearly no similar blood vessel.

100% spreading rate reflects that the high-speed blood flow in sepsis is activated relatively completely, and merely 1% spreading rate reflects that the high-speed blood flow is being in an activated state or vanishing state. The same is applicable to other similitudes.

The flow rate in the capillaries of the healthy person within the field of view also has similarity and dissimilarity (heterogeneity), while a key difference between the blood flow rate in the capillaries of the healthy person and the blood flow rate in sepsis is whether the highest blood flow rate exceeds the limit of the healthy person.

Meanwhile, an absolute value of the high-speed blood flow rate in an activated stage and a declining stage will be less than 1500 μm, and the spreading rate also will be nearly the same as that of the normal blood flow of the healthy person. In this case, comprehensive tracing and judgment is particularly needed in combination with other symptoms of the patient.

The quantitative analysis parameters include the high-speed blood flow intensity duration.

This parameter is mainly used to trace and track the possible historical time of occurrence of the high-speed blood flow and judge the possible approaching time of the infectious shock.

The high-speed blood flow intensity duration refers to a time interval between the time when the high-speed blood flow is found for the first time and the time when the high-speed blood flow begins to decelerate (The same blood vessel within the same field of view is observed conditionally in the hospital, and the tracking time is substantially determined according to complaints of the patient).

The high-speed blood flow intensity duration is: $T=T2-T1$ (with respect to the same blood vessel within the same field of view), T is the high-speed blood flow intensity duration; T1 is the time when the high-speed blood flow is found for the first time, and it also can be traced and judged according to other manifestations of the patient (for example, the initial onset time or the like).

T2 is the time when the high-speed blood flow begins to decelerate.

If it is found that too long duration of the high-speed blood flow intensity (take caution if the duration is greater than 4 hours) will cause fatigue or even paralysis of capillary sphincter and smooth muscle, and finally cause lots of blood to enter true capillaries which are not open normally, resulting in insufficient effective blood volume, and sudden drop of the blood pressure—the infectious shock occurs. Therefore, knowing the high-speed blood flow duration T facilitates judging the progress of the condition. Due to low toxicity, common viruses will not simulate the continuous generation of the high-speed blood flow intensity and thus will not finally lead to the paralysis of sphincter and smooth muscle. However, the septic shock is caused by complete paralysis of sphincter and smooth muscle that is finally resulted from strong toxicity and continuous generation of the toxin. Therefore, by observing the duration of the high-speed blood flow intensity, the probability of occurrence of the shock can be predicted. This index also explains why some patients with sepsis will not suffer from shock. This is because these patients are physically strong with relatively powerful sphincter and smooth muscle, or antibodies in their bodies eliminate endotoxins, thus the shock will not occur since the effects of the endotoxins fail to cause paralysis of the smooth muscle and sphincter.

The quantitative analysis indices include the difference of abnormal change in high-speed blood flow intensity.

This parameter is mainly used to judge the presence of the high-speed blood flow and different stages of the infectious shock. Since the sublingual blood flow of a healthy person is generally in a constant flow state when the person does not do strenuous exercise, the abnormal acceleration and abnormal deceleration of the blood flow rate will not occur to a healthy person. The occurrence of such situation (the abnormal acceleration and abnormal deceleration), even if the blood flow rate is not very high, is the fourth specific index of the infectious shock. The abnormal acceleration of the flow rate reflects an activation stage of the high-speed blood flow of the early stage of the infectious shock, and the abnormal deceleration of the flow rate reflects that the infectious shock is at the middle and advanced stages.

The difference of abnormal change in high-speed blood flow intensity refers to the acceleration change of the high-speed blood flow rates of the sublingual microcirculation of a patient with infectious shock, i.e., abnormal acceleration or abnormal deceleration of the high-speed blood flow rates of the sublingual microcirculation of the patient with infectious shock within different periods of time.

The difference of abnormal change in high-speed blood flow intensity is: $D=D1-D2$.

D is the difference of abnormal change in high-speed blood flow intensity of the patient with infectious shock D1 is a difference of changes in highest blood flow rate of the patient with infectious shock.

D2 is a difference of changes in highest blood flow rate of the healthy person.

The difference of changes in highest blood flow rate of the patient with infectious shock is $D1=P2-P1$.

P2 is an average of last measured highest blood flow rates of the patient with infectious shock.

P1 is an average of previously measured highest blood flow rates of the patient with infectious shock.

If D1 is greater than 0, it means that the blood flow rate is accelerated; if D1 is less than 0, it means that the blood flow rate is decelerated; if D1 is equal to 0, it means that the blood flow rate is stable.

$$D2=P4-P3.$$

D2 is a difference of changes in highest blood flow rate of the healthy person.

P4 is an average of last measured highest blood flow rates of the healthy person.

P3 is an average of previously measured highest blood flow rates of the healthy person.

(This numerical value is generally equal to 0, that is to say, the sublingual blood flow of a healthy person is generally in a constant flow state when the person does not do strenuous exercise).

Since the sublingual blood flow of a healthy person is generally in the constant flow state when the person does not do strenuous exercise, actually, the difference D of abnormal change in high-speed blood flow intensity is equal to the difference D1 of changes in highest blood flow rate of the patient with infectious shock, that is, $D=D1$.

The formula is simplified as $D=D1-D2=P2-P1$, i.e., a difference between averages of the last and previous high-speed blood flow rates of the same blood vessel in the sublingual microcirculation of the patient with infectious shock.

If D and D1 are greater than 0, it means that the blood flow rate is accelerated, if D and D1 are less than 0, it means that the blood flow rate is decelerated; if D and D1 are equal to 0, it means that the flow rate is stable.

Since the blood flow rate of a healthy person is stable, $P4-P3=0$, then, the difference of abnormal changes in high-speed blood flow intensity of a monitored object is $D=D1-D2=D1=P2-P1$, that is, equal to a difference between a real-time average P2 of highest blood flow rates of the patient and the previously measured average P1 of highest blood flow rates in the same blood vessel in the same area.

The following two points need to be noted:

1. the indices above are comparison data of the same blood vessel within the same field of view in a previous period of time and a later period of time; and 2. different normal values of the highest blood flow rates in the normal sublingual circulation should be established for different ages, genders and races, so as to facilitate the comparison with the high-speed blood flow intensity.

The four specific indices are very useful and associated with each other. In the examination of the early and middle stage of sepsis, if the first specific index and the second specific index are found—high-speed blood flow is suspected, and meanwhile the high-speed blood flow spreading rate is very high, close attention needs to be paid. Over time, if it is found that the third specific index—the duration T of the high-speed blood flow intensity (observed at the same blood vessel parts)—exceeds 4 hours, more attention should be paid to the probability of the shock. According to the fourth index—abnormal acceleration or abnormal deceleration—in combination other sepsis symptoms, in the case of no any rescue, the early or middle stage sepsis and the development trend of the disease can be determined, thus the timely rescue is provided.

During the observation of the high-speed blood flow intensity, the following points should be noted.

(1) The objects observed herein are different from the observed objects mentioned in the international round table conference where small blood vessels having a diameter of no more than 20 μm are used as observed objects. Herein, one blood vessel at the fastest flow rate within the microscopic field of view is selected (it is possible to select the fastest blood vessel upon comparison of 3-5 observation points). Generally, the thickness of the blood vessels is not taken into consideration. However, it is preferred to select blood vessels greater than 20 μm to 25 μm in diameter because the flow rate in the large blood vessels is relatively stable, difficult to disappear, and rarely affected by the pressure of the probe. In the case where large and small blood vessels substantially have the same highest blood flow rate, the largest blood vessels are preferred as samples for calculating the blood flow rate. In the observation, it is best to select no less than two such blood vessels with the fastest blood flow rate within the field of view.

(2) At least no less than two parts can be selected for observation and sampling.

(3) The high-speed blood flow can be found in the early and middle stages of sepsis, and the high-speed blood flow disappears in the advanced stage. If the spreading rate is low, it means that the high-speed blood flow is just activated in the early stage of sepsis or the sepsis has been under way to the middle and advanced stages, and there is a heterogeneous blood flow phenomenon (the difference between the high-speed blood flow rate and the low-speed blood flow rate is very large). If lots of blood is retained, it means that the patient is under way to the advanced stage. The highest blood flow rate of the high-speed blood flow is not significant when the high-speed blood flow slows down or is just activated, then comprehensive judgment should be made in combination with other symptoms.

(4) The comparison must to be conducted with respect to the same blood vessel in the same area within different periods of time.

(5) These indices must be jointly used with other sepsis indices.

Further, the storage module includes a blood flow rate quick-matching sample template, and the blood flow rate quick-matching sample template includes a set of flow rate video templates on which flow rates are accurately marked, for quickly comparing and judging the flow rate in the blood vessel from the real-time blood vessel image data. Just upon comparison with these templates, a user can quickly judge the blood flow rate of an actual case, without the needs of calculating the blood flow rate of the patient every time.

For example, the blood flow rate quick-matching sample templates are numbered by A1, A2, A3 . . . .

In the above, A1, the highest blood flow rate within the field of view is 800 µm/s, In A2, the highest blood flow rate within the field of view is 1000 µm/s, In A3, the highest blood flow rate within the field of view is 1200 µm/s In A4, the highest blood flow rate within the field of view is 1400 µm/s In A5, the highest blood flow rate within the field of view is 1600 µm/s In A6, the highest blood flow rate within the field of view is 1800 µm/s In A7, the highest blood flow rate within the field of view is 2000 µm/s In A8, the highest blood flow rate within the field of view is 2200 µm/s In A9, the highest blood flow rate within the field of view is 2400 µm/s In A10, the highest blood flow rate within the field of view is 2600 µm/s In A11, the highest blood flow rate within the field of view is 2800 µm/s In A12, the highest blood flow rate within the field of view is 3000 µm/s, As long as an operator roughly judges the blood flow rate currently seen, the operator can call the template with similar rate for comparison, without the need of performing tedious calculation of the rate, thus achieving the object of quickly obtaining a result.

An embodiment of a method for monitoring the high-speed blood flow intensity, similarity, high-speed blood flow intensity duration and the difference of the abnormal strength change thereof in the microcirculation for shock monitoring is described below.

It includes the following steps:

repeatedly positioning the same blood vessel in the same monitored area and acquiring blood vessel image data;

filtering and stabilizing the acquired blood vessel image data;

storing measured blood vessel image data and reference data in a database; and comparing the measured blood vessel image data (data having been stabilized) with the reference data, and judging and analyzing changes in flow rate in the blood vessel and/or changes in distribution density of the blood vessel.

Preferably, the range of observation of the present invention is the blood vessels in the sublingual mucosal microcirculation and the fundus retinal microcirculation.

Further, in the method for monitoring blood vessels in the microcirculation for shock monitoring, the step of judging and analyzing is as follows:

in comparing the blood vessel images (data having been stabilized), taking the real-time blood vessel image data as the measured data, taking the data of the same blood vessel in the same previously monitored area having undergone the blood vessel image stabilization as the reference data, and judging the change in blood flow rate in the blood vessel and/or the density change upon the operator's observation with naked eyes.

Further, in the method for monitoring blood vessels in a microcirculation for shock monitoring, the step of judging and analyzing is as follows:

measuring the flow rate of the blood flow after the step of filtering and stabilizing the acquired blood vessel image data, for generating real-time flow rate in the blood vessel.

The data stored in the database includes the real-time data and historical data of blood vessel images of the monitored object, average data of highest microcirculation blood flow rates of a healthy person, difference data of changes in blood flow rates of a healthy person, and stabilized data of the above data.

In comparing the blood vessel images (data having been stabilized), four quantitative analysis indices are involved.

A first quantitative analysis index is high-speed blood flow intensity ratio R: $R=P/N*100\%$, where the average P of highest blood flow rates of the monitored object within a certain period of time is taken as the measured data, the data of the average N of highest blood flow rates in the microcirculation of a healthy person is taken as the reference data.

This index is mainly used to evaluate the strength of the high-speed blood flow.

The high-speed blood flow intensity ratio is a ratio of an average of highest blood flow rates in the sublingual microcirculation of a patient with infectious shock within the field of view to an average of highest blood flow rates in a sublingual microcirculation of a healthy person.

The high-speed blood flow intensity ratio R is $R=P/N*100\%$,

R is the high-speed blood flow intensity ratio.

P is the average of highest blood flow rates in the sublingual microcirculation of the patient with infectious shock within the field of view (prestissimo).

N is the average of highest blood flow rates in the sublingual microcirculation of the healthy person (normal).

The greater this ratio is, the higher the high-speed blood flow intensity is, and the higher the blood flow rate is. The occurrence of the high-speed blood flow intensity indicates that the toxin is highly toxic and is difficult to be deactivated by the blood itself, so that the brain activates the high-speed blood flow to quickly convey the toxin to the liver for detoxification. The occurrence of the high-speed blood flow indicates possible development of infectious shock (sepsis).

An example is as follows:

Actual measurement: an average of highest blood flow rates of two blood vessels of a patient with infectious shock is 3000 μm/s, and the normal value of the average of highest blood flow rates of a healthy person is 1000 μm/s, then the high-speed blood flow intensity ratio is R=3000(P)/1000(N) *100%=300%, i.e., three times of that of the normal value.

If the average of highest blood flow rates of two blood vessels of a patient with infectious shock is P=150 μm/s, and the normal value is N=1000 μm/s, the high-speed blood flow intensity ratio is R=150(P)/1000(N)*100%=0.25*100%= 15%, i.e., the highest blood flow rate of this patient is equivalent to 15% of the normal value.

A second quantitative analysis parameter is high-speed blood flow spreading rate (S)=(the total length of the high-speed blood flow/the total length of all blood vessels) within the field of view*100%

The high-speed blood flow spreading rate is S=HL/TL.

S=high-speed blood flow similarity.

HL=total length of all blood vessels at a high-speed blood flow rate within the field of view.

TL=total length of all blood vessels within the same field of view.

(In order to simplify the calculation, the microcirculation blood flow rate can be classified according to the classification method in the international round table conference in 2007: retention=1, intermittent flow=1, slow flow=2, continuous flow=3, and high-speed flow=4.)

Example 1 if the total length of all blood vessels within the field of view is 6000 μm and the blood flow in all capillaries is high-speed blood flow, then the total length of the high-speed blood flow is also 6000 μm, then spreading rate (S)=6000/6000=1*100%=100%, which indicates complete similitude.

Example 2 if the total length of all blood vessels within the field of view is 8600 μm and the total length of the high-speed blood flow therein is 4300 μm, then spreading rate (S)=4300/8600=0.5*100%=50%, which indicates semi-similitude.

Example 3 if the total length of all blood vessels within the field of view is 10000 μm and the total length of the high-speed blood flow therein is 100 μm, then spreading rate (S)=100/10000=0.01*100%=1%, which indicates that there is nearly no similar blood vessel.

100% spreading rate reflects that the high-speed blood flow in sepsis is activated relatively completely, and merely 1% spreading rate reflects that the high-speed blood flow is being in an activated state or vanishing state. The same is applicable to other similitudes.

The flow rate in the capillaries of the healthy person within the field of view also has similarity and dissimilarity (heterogeneity), while a key difference between the blood flow rate in the capillaries of the healthy person and the blood flow rate in sepsis is whether the highest blood flow rate exceeds the limit of the healthy person.

Meanwhile, an absolute value of the high-speed blood flow rate in an activated stage and a declining stage will be less than 1500 μm, and the spreading rate also will be nearly the same as that of the normal blood flow of the healthy person. In this case, comprehensive tracing and judgment is particularly needed in combination with other symptoms of the patient.

A third quantitative analysis parameter is high-speed blood flow intensity duration T.

This parameter is mainly used to trace and track the possible historical time of occurrence of the high-speed blood flow and judge the possible approaching time of the infectious shock.

The high-speed blood flow intensity duration refers to a time interval between the time when the high-speed blood flow is found for the first time and the time when the high-speed blood flow begins to decelerate (The same blood vessel within the same field of view is observed conditionally in the hospital, and the tracking time is substantially determined according to complaints of the patient).

The high-speed blood flow intensity duration is: T=T2−T1 (with respect to the same blood vessel within the same field of view), T is the high-speed blood flow intensity duration; T1 is the time when the high-speed blood flow is found for the first time, and it also can be traced and judged according to other manifestations of the patient (for example, the initial onset time or the like).

T2 is the time when the high-speed blood flow begins to decelerate.

If it is found that too long duration of the high-speed blood flow intensity (take caution if the duration is greater than 4 hours) will cause fatigue or even paralysis of capillary sphincter and smooth muscle, and finally cause lots of blood to enter true capillaries which are not open normally, resulting in insufficient effective blood volume, and sudden drop of the blood pressure—the infectious shock occurs. Therefore, knowing the high-speed blood flow duration T facilitates judging the progress of the condition. Due to low toxicity, common viruses will not simulate the continuous generation of the high-speed blood flow intensity and thus will not finally lead to the paralysis of sphincter and smooth muscle. However, the septic shock is caused by complete paralysis of sphincter and smooth muscle that is finally resulted from strong toxicity and continuous generation of the toxin. Therefore, by observing the duration of the high-speed blood flow intensity, the probability of occurrence of the shock can be predicted. This index also explains why some patients with sepsis will not suffer from shock. This is because these patients are physically strong with relatively powerful sphincter and smooth muscle, or antibodies in their bodies eliminate endotoxins, thus the shock will not occur since the effects of the endotoxins fail to cause paralysis of the smooth muscle and sphincter.

A fourth quantitative analysis index is difference of abnormal change in high-speed blood flow intensity.

This parameter is mainly used to judge the presence of the high-speed blood flow and different stages of the infectious shock. Since the sublingual blood flow of a healthy person is generally in a constant flow state when the person does not do strenuous exercise, the abnormal acceleration and abnormal deceleration of the blood flow rate will not occur to a healthy person. The occurrence of such situation (the abnormal acceleration and abnormal deceleration), even if the blood flow rate is not very high, is the fourth specific index of the infectious shock. The abnormal acceleration of the flow rate reflects an activation stage of the high-speed blood flow of the early stage of the infectious shock, and the abnormal deceleration of the flow rate reflects that the infectious shock is at the middle and advanced stages.

The difference of abnormal change in high-speed blood flow intensity refers to the acceleration change of the high-speed blood flow rates of the sublingual microcirculation of a patient with infectious shock, i.e., abnormal acceleration or abnormal deceleration of the high-speed blood flow rates of the sublingual microcirculation of the patient with infectious shock within different periods of time.

The difference of abnormal change in high-speed blood flow intensity is D=D1−D2.

D is the difference of abnormal change in high-speed blood flow intensity.

D1 is a difference of changes in highest blood flow rate of the patient with infectious shock.

D2 is a difference of changes in highest blood flow rate of the healthy person.

The difference of changes in highest blood flow rate of the patient with infectious shock is D1=P2−P1.

P2 is the average of last measured highest blood flow rates of the patient with infectious shock.

P1 is the average of previously measured highest blood flow rates of the patient with infectious shock.

If D1 is greater than 0, it means that the blood flow rate is accelerated; if D1 is less than 0, it means that the blood flow rate is decelerated; if D1 is equal to 0, it means that the blood flow rate is stable.

$$D2=P4-P3.$$

D2 is a difference of changes in highest blood flow rate of the healthy person.

P4 is the average of last measured highest blood flow rates of the healthy person.

P3 is the average of previously measured highest blood flow rates of the healthy person.

(This numerical value is generally equal to 0, that is to say, the sublingual blood flow of a healthy person is generally in a constant flow state when the person does not do strenuous exercise).

Since the sublingual blood flow of a healthy person is generally in the constant flow state when the person does not do strenuous exercise, actually, the difference D of the abnormal changes in blood flow rate of a patient with infectious shock is equal to the difference D1 of changes in highest blood flow rate of the patient with infectious shock, that is, D=D1.

The formula is simplified as D=D1−D2=P2−P1, i.e., a difference between averages of the last and previous high-speed blood flow rates of the same blood vessel in the sublingual circulation of the patient with infectious shock.

If D and D1 are greater than 0, it means that the blood flow rate is accelerated; if D and D1 are less than 0, it means that the blood flow rate is decelerated; if D and D1 are equal to 0, it means that the flow rate is stable.

Since the blood flow rate of a healthy person is stable, P4-P3 is equal to 0, then, the difference of the abnormal change in high-speed blood flow intensity of the monitored object is D=D1−D2=D1=P2−P1, that is, equal to a difference between a real-time highest blood flow rate P2 of the patient and the previously measured highest blood flow rate P1 in the same blood vessel in the same area.

An example is as follows:

Actual measurement:

With the above inventive device, data of same blood vessels are acquired at same positions of the sublingual microcirculation of a patient with infectious shock in different periods of time. For example, an average flow rate P1 of highest flow rates of acquired blood vessels A and B is 1200 μm/s at 10:00 A.M.; and an average flow rate P2 of highest flow rates of the acquired blood vessels A and B is 2200 μm/s at 12:00 A.M., then The difference D1 of the highest blood flow rate change of the patient suspected with septic shock is D1=2200(P2)−1200(P1)=+1000 μm/s.

D2 is equal to a difference between the real-time blood flow rate P4 of a healthy person and the previously measured blood flow rate P3 (the highest blood flow rate in the same blood vessel within the same field of view).

D2=580(P4)−580(P3)=0 means that the healthy person has a constant blood flow rate.

Therefore, the difference D of the abnormal change in high-speed blood flow intensity is D=+1000(D1)−0(D2)=+1000 μm/s, indicating that the blood flow rate of the patient is accelerated (the blood flow rate in the microcirculation of a healthy person is constant).

For another patient suspected with infectious shock, an average flow rate P1 of acquired blood vessels A and B is 3200 μm/s at 3:00 P.M. and an average flow rate P2 of the acquired blood vessels A and B is 450 μm/s, at 6:00 P.M., then, the difference D1 of changes in highest blood flow rate of the patient with infectious shock is: D1=450(P2)−3200(P1)=−2750 μm/s.

Therefore, the difference D of abnormal change in high-speed blood flow intensity is D=−2750 μm/s (D1)−0(D2)−2750 μm/s, a negative value, indicating that the blood flow slows down (The difference of the abnormal change in the highest blood flow rate in the sublingual microcirculation of a healthy person is 0).

The following two points need to be noted:

1. the indices above are comparison data of the same blood vessel within the same field of view in a previous period of time and a later period of time.

2. different normal values of the highest blood flow rates in the normal sublingual circulation should be established for different ages, genders and races, so as to facilitate the comparison with the high-speed blood flow intensity.

The four specific indices are very useful and associated with each other. In the examination of the early and middle stage of sepsis, if the first specific index and the second specific index are found—high-speed blood flow is suspected, and meanwhile the high-speed blood flow spreading rate is very high, close attention needs to be paid. Over time, if it is found that the third specific index—the duration T of the high-speed blood flow intensity (observed at the same blood vessel parts)—exceeds 4 hours, more attention should be paid to the probability of the shock. According to the fourth index—abnormal acceleration or abnormal deceleration—in combination other sepsis symptoms, in the case of no any rescue, the early or middle stage sepsis and the development trend of the disease can be determined, thus the timely rescue is provided.

During the observation of the high-speed blood flow intensity, the following points should be noted.

(1) The objects observed herein are different from the observed objects mentioned in the international round table conference where small blood vessels having a diameter of no more than 20 μm are used as observed objects. Herein, one blood vessel at the fastest flow rate within the microscopic field of view is selected (it is possible to select the fastest blood vessel upon comparison of 3-5 observation points). Generally, the thickness of the blood vessels is not taken into consideration. However, it is preferred to select blood vessels greater than 20 μm to 25 μm in diameter because the flow rate in the large blood vessels is relatively stable, difficult to disappear, and rarely affected by the pressure of the probe. In the case where large and small blood vessels substantially have the same highest blood flow rate, the largest blood vessels are preferred as samples for calculating the blood flow rate. In the observation, it is best to select no less than two such blood vessels with the fastest blood flow rate within the field of view.

(2) At least no less than two parts can be selected for observation and sampling, and a part at the highest rate within the field of view is selected after comparison.

(3) The high-speed blood flow can be found in the early and middle stages of sepsis, and the high-speed blood flow disappears in the advanced stage. If the spreading rate is low, it means that the high-speed blood flow is just activated in the early stage of sepsis or the sepsis has been under way to the middle and advanced stages, and there is a heterogeneous blood flow phenomenon (the difference between the high-speed blood flow rate and the low-speed blood flow rate is very large). If lots of blood is retained, it means that the patient is under way to the advanced stage. The highest blood flow rate of the high-speed blood flow is not significant when the high-speed blood flow slows down or is just activated, then comprehensive judgment should be made in combination with other symptoms.

(4) The comparison must to be conducted with respect to the same blood vessel in the same area within different periods of time.

(5) These indices must be jointly used with other sepsis indices.

The forgoing embodiments are merely for some preferred implementations of the present invention. All general alterations and replacements made by those skilled in the art within the scope of the technical solutions of the present invention shall fall into the scope of protection of the present invention.

What is claimed is:

1. A microcirculation shock monitor enabling rapid and repeated positioning, comprising a host body,
wherein a front end of the host body is mounted with a probe device, the host body is internally provided with a microscope continuous zooming mechanism, two ends of the microscope continuous zooming mechanism are respectively mounted with a front lens and a rear lens, the rear lens is directly connected to a camera, and at least one zooming lens capable of reciprocating along a direction of a zooming mechanism driving and guiding device is provided between the front lens and the rear lens.

2. The microcirculation shock monitor enabling rapid and repeated positioning according to claim 1, wherein a focusing tube is mounted in a rear portion of the probe device or on the front lens of the microscope continuous zooming mechanism or on the camera.

3. The microcirculation shock monitor enabling rapid and repeated positioning according to claim 1, wherein a direction adjustment mechanism and/or a parfocalization mechanism and/or a cross calibration mechanism is mounted between the microscope continuous zooming mechanism and the camera.

4. The microcirculation shock monitor enabling rapid and repeated positioning according to claim 1, wherein the host body is provided with a probe sleeve at the front end, the probe device is mounted on the probe sleeve in a way of being movable relative to the host body in an axial movement direction, and an adjustment and positioning device is mounted between the probe sleeve and the probe device.

5. The microcirculation shock monitor enabling rapid and repeated positioning according to claim 1, wherein a handle is further provided on the host body for facilitating holding and controlling a viewing angle.

6. The microcirculation shock monitor enabling rapid and repeated positioning according to claim 1, wherein a disposable sterile sheath is provided on the probe device.

7. A microcirculation shock monitoring system, comprising:
a data acquisition device, configured to repeatedly position the a blood vessel in a monitored area and acquire blood vessel image data;
a data preprocessor configured to filter and stabilize the acquired blood vessel image data;
a comparison processor, configured to compare measured stabilized blood vessel image data with reference data, to judge and analyze changes in a blood flow rate in the blood vessel and/or changes in distribution density of the blood vessel; and
a storage device, configured to store the measured blood vessel image data and the reference data in a database;
wherein in the processor, one or more of the following quantitative analysis parameters includes:
i) high-speed blood flow intensity ratio, referring to a ratio of an average of highest blood flow rates in a sublingual microcirculation of a patient with infectious shock within a field of view to an average of highest rates in a sublingual microcirculation of a healthy person;
the high-speed blood flow intensity ratio is $R=P/N*100\%$,
wherein P is the average of highest blood flow rates in the sublingual microcirculation of the patient with infectious shock within the field of view; and
N is the average of highest blood flow rates in the sublingual microcirculation of the healthy person;
the high-speed blood flow intensity ratio is used to evaluate strength of a high-speed blood flow;
ii) high-speed blood flow similarity, referring to a ratio of a total length of all blood vessels at a high blood flow rate to a total length of all capillaries in the sublingual microcirculation of a patient with infectious shock within the field of view;
the high-speed blood flow spreading rate is $S=HL/TL*100\%$,
where HL is the total length of all blood vessels at a high-speed blood flow rate within the field of view, and
TL is the total length of all blood vessels within the field of view; and
the high-speed blood flow spreading rate is used to evaluate whether the high-speed blood flow is activated completely;
iii) high-speed blood flow intensity duration, referring to a time interval between a time when a high-speed blood flow is found in a sublingual microcirculation of a patient with infectious shock for a first time and a time when the high-speed blood flow begins to decelerate;
the high-speed blood flow intensity duration is $T=T2-T1$,
where T is the high-speed blood flow intensity duration; T1 is the time when the high-speed blood flow is found for the first time, and T1 also can be traced and judged according to other manifestations of the patient,
T2 is the time when the high-speed blood flow begins to decelerate; and
the high-speed blood flow intensity duration is used to trace and track a possible historical occurrence time of the high-speed blood flow, to judge a possible approaching time of the infectious shock; and iv) difference of abnormal change in high-speed blood flow intensity, referring to acceleration change of the high-speed blood flow rates of the sublingual microcirculation of a patient with infectious shock, the difference of abnormal change in high-speed blood flow intensity is D=D1−D2, where D is a difference of abnormal change in high-speed blood flow intensity of the patient with infectious shock, D1 is a difference of changes in highest blood flow rate of the patient with infectious shock, D2 is a difference of changes in highest blood flow rate of a healthy person, the difference of changes in the highest blood flow rate of the patient with infectious shock is D1=P2−P1, where P2 is an average of last measured highest blood flow rates of the patient with infectious shock;

P1 is an average of previously measured highest blood flow rates of the patient with infectious shock;

if D1 is greater than 0, the blood flow rate is accelerated; if D1 is less than 0, the blood flow rate is decelerated; if D1 is equal to 0, the blood flow rate is stable;

$$D2=P4-P3,$$

where D2 is a difference of changes in highest blood flow rate of the healthy person;

P4 is an average of last measured highest blood flow rates of the healthy person;

P3 is an average of previously measured highest blood flow rates of the healthy person; and the difference of abnormal change in high-speed blood flow reflects abnormal acceleration change of the high-speed blood flow.

8. The microcirculation shock monitoring system according to claim 7, wherein the data preprocessor comprises a blood flow rate measurement device, configured to generate real-time flow rate data in the blood vessel; and data stored in the storage device comprises real-time data and historical data of blood vessel images of a monitored object, average data of highest microcirculation blood flow rates of a healthy person, and difference data of changes in blood flow rates of the healthy person, and stabilized data of said data.

9. The microcirculation shock monitoring system according to claim 7, wherein the storage device comprises a blood flow rate quick-matching sample template, and the blood flow rate quick-matching sample template comprises a set of flow rate video templates on which flow rates are accurately marked, for quickly comparing and judging the flow rate in the blood vessel from real-time blood vessel image data.

10. A method for monitoring blood flow change parameters in blood vessels in microcirculation for shock monitoring, comprising:

repeatedly positioning a blood vessel in a monitored area and acquiring blood vessel image data;

filtering and stabilizing the acquired blood vessel image data;

storing measured blood vessel image data and reference data in a database; and comparing the measured blood vessel image data having been stabilized with the reference data, and judging and analyzing changes in flow rate in the blood vessel and/or changes in distribution density of the blood vessel;

wherein the step of judging and analyzing comprises:
measuring the flow rate of the blood flow after the step of filtering and stabilizing the acquired blood vessel image data, for generating a real-time flow rate in the blood vessel;

wherein data stored in the database comprises real-time data and historical data of blood vessel images of a monitored object, average data of highest microcirculation blood flow rates of a healthy person, difference data of changes in blood flow rates of the healthy person, and stabilized data of said data;

wherein, in comparing the measured blood vessel image data, four quantitative analysis indices are used:

i) a first quantitative analysis parameter is high-speed blood flow intensity ratio:

the high-speed blood flow intensity ratio refers to a ratio of an average of highest blood flow rates in sublingual microcirculation of a patient with infectious shock within a field of view to an average of highest blood flow rates in a sublingual microcirculation of the healthy person;

wherein the high-speed blood flow intensity ratio is R=P/N*100%, where P is the average of highest blood flow rates in the sublingual microcirculation of the patient with infectious shock within the field of view; and N is the average of highest blood flow rates in the sublingual microcirculation of the healthy person; and the high-speed blood flow intensity ratio is used to evaluate the high-speed blood flow intensity;

ii) a second quantitative analysis parameter is high-speed blood flow similarity:

the high-speed blood flow similarity refers to a ratio of a total length of all blood vessels at a high blood flow rate to a total length of all capillaries in the sublingual microcirculation of the patient with infectious shock within the field of view;

the high-speed blood flow spreading rate is S=HL/TL*100%, where HL is the total length of all blood vessels at a high blood flow rate within the field of view, and TL is the total length of all blood vessels within the field of view; and the high-speed blood flow spreading rate is used to evaluate whether the high-speed blood flow is activated completely;

iii) a third quantitative analysis parameter is high-speed blood flow intensity duration:

the high-speed blood flow intensity duration refers to a time interval between a time when the high-speed blood flow is found for the first time in the sublingual microcirculation of the patient with infectious shock and a time when the high-speed blood flow begins to decelerate;

$$T=T2-T1,$$

where T is the high-speed blood flow intensity duration; T1 is the time when the high-speed blood flow is found for the first time, and also can be traced and judged according to other manifestations of the patient, T2 is the time when the high-speed blood flow begins to decelerate; and the high-speed blood flow intensity duration is used to trace and track a possible historical time of occurrence of the high-speed blood flow and judge a possible approaching time of the infectious shock; and iv) a fourth quantitative analysis index is a difference of abnormal change in high-speed blood flow intensity;

the difference of abnormal change in high-speed blood flow intensity refers to acceleration change of the high-speed blood flow rates of the sublingual microcirculation of the patient with infectious shock;

the difference of abnormal change in high-speed blood flow intensity is D=D1−D2, where D is the difference of abnormal change in high-speed blood flow intensity of the patient with infectious shock, D1 is the difference of changes in highest blood flow rate of the patient with infectious shock, D2 is the difference of changes in highest blood flow rate of the healthy person, the difference of changes in highest blood flow rate of the patient with infectious shock is D1=P2−P1, where P2 is an average of last measured highest blood flow rates of the patient with infectious shock;

P1 is an average of previously measured highest blood flow rates of the patient with infectious shock;

if D1 is greater than 0, the blood flow rate is accelerated;
if D1 is less than 0, the blood flow rate is decelerated;
if D1 is equal to 0, the blood flow rate is stable;

$D2=P4-P3$, where D2 is a difference of changes in highest blood flow rate of the healthy person;

P4 is an average of last measured highest blood flow rates of the healthy person;

P3 is an average of previously measured highest blood flow rates of the healthy person; and the difference of abnormal change in high-speed blood flow mainly reflects abnormal acceleration change of the high-speed blood flow.

11. The method for monitoring blood flow change parameters in blood vessels in microcirculation for shock monitoring according to claim 10, wherein the step of judging and analyzing is as follows:

in comparing the measured blood vessel image data, taking real-time blood vessel image data having been stabilized as the measured data, taking the data of the blood vessel image data of the blood vessel in the monitored area having undergone stabilization as the reference data, and judging a change in flow rate in the blood vessel and/or a density change upon an operator's observation with naked eyes.

* * * * *